(12) United States Patent
Inoue et al.

(10) Patent No.: US 11,026,942 B2
(45) Date of Patent: Jun. 8, 2021

(54) AGENT FOR PREVENTING AND/OR TREATING ALZHEIMER'S DISEASE

(71) Applicant: KYOTO UNIVERSITY, Kyoto (JP)

(72) Inventors: Haruhisa Inoue, Kyoto (JP); Takayuki Kondo, Kyoto (JP)

(73) Assignee: KYOTO UNIVERSITY, Kyoto (JP)

(*) Notice: Subject to any disclaimer, the term of this patent is extended or adjusted under 35 U.S.C. 154(b) by 0 days.

(21) Appl. No.: 16/066,946

(22) PCT Filed: Dec. 29, 2016

(86) PCT No.: PCT/JP2016/089217
§ 371 (c)(1),
(2) Date: Jun. 28, 2018

(87) PCT Pub. No.: WO2017/115873
PCT Pub. Date: Jul. 6, 2017

(65) Prior Publication Data
US 2019/0008860 A1     Jan. 10, 2019

(30) Foreign Application Priority Data

Dec. 29, 2015 (JP) .............................. JP2015-257706

(51) Int. Cl.
| | | |
|---|---|---|
| *A61K 31/4985* | (2006.01) | |
| *A61K 45/06* | (2006.01) | |
| *A61K 31/352* | (2006.01) | |
| *A61K 31/353* | (2006.01) | |
| *A61P 25/28* | (2006.01) | |
| *A61K 31/357* | (2006.01) | |
| *A61K 31/405* | (2006.01) | |
| *A61K 31/4709* | (2006.01) | |
| *A61K 31/404* | (2006.01) | |
| *A61K 31/10* | (2006.01) | |
| *A61K 31/48* | (2006.01) | |
| *A61K 31/7048* | (2006.01) | |
| *A61K 31/095* | (2006.01) | |

(52) U.S. Cl.
CPC ........ *A61K 31/4985* (2013.01); *A61K 31/095* (2013.01); *A61K 31/10* (2013.01); *A61K 31/352* (2013.01); *A61K 31/353* (2013.01); *A61K 31/357* (2013.01); *A61K 31/404* (2013.01); *A61K 31/405* (2013.01); *A61K 31/4709* (2013.01); *A61K 31/48* (2013.01); *A61K 31/7048* (2013.01); *A61K 45/06* (2013.01); *A61P 25/28* (2018.01)

(58) Field of Classification Search
CPC .............. A61K 31/407; A61K 31/4985; A61K 31/075; A61K 31/357; A61P 25/28
See application file for complete search history.

(56) References Cited

U.S. PATENT DOCUMENTS

| | | | |
|---|---|---|---|
| 8,809,302 B2 * | 8/2014 | Cohen .................. | A61K 31/137 514/56 |
| 2012/0270836 A1 | 10/2012 | Cohen et al. | |
| 2013/0085122 A1 | 4/2013 | Cohen et al. | |
| 2013/0090307 A1 * | 4/2013 | Cohen .................. | A61K 31/137 514/56 |
| 2014/0140927 A1 * | 5/2014 | Elmaleh ............... | C07D 311/24 424/1.89 |

FOREIGN PATENT DOCUMENTS

| | | | |
|---|---|---|---|
| JP | 2013-510114 A | 3/2013 | |
| JP | 2014-506909 A | 3/2014 | |
| WO | WO-2011054759 A1 * | 5/2011 | ........... A61K 31/137 |

OTHER PUBLICATIONS

Becker et al., J. Alzheimer's Disease vol. 15 pp. 303-325, published 2008 (Year: 2008).*
Shi et al (CNS Neuroscience and Therapeutics vol. 19 pp. 871-881 published 2013) (Year: 2013).*
Becker et al (Why do so many drugs for Alzheimer's disease fail in development? J. Alzheimer's Disease vol. 15 pp. 303-325, published 2008 (Year: 2008).*
Greicius et al. (J Neurol. Neurosurg. Psychiatry, Jun. 2002; 72(6):691-700) (Year: 2002).*
Gasparini et al. (FASEB J., Jan. 12, 1998, pp. 17-34). (Year: 1998).*
Ono et al (Neurochemistry International vol. 48 pp. 275-285. Published 2006). (Year: 2006).*
Corbett et al., "Drug repositioning in Alzheimer's disease," *Front. Biosci. (Schol. Ed.)*, 7: 184-188 (2015).
Hori et al., "A Food and Drug Administration-approved Asthma Therapeutic Agent Impacts Amyloid β in the Brain in a Transgenic Model of Alzheimer Disease," *J. Biol. Chem.*, 290(4): 1966-1978 (2015).
Liu et al., "Effect of Potent γ-Secretase Modulator in Human Neurons Derived From Multiple Presenilin 1-Induced Pluripotent Stem Cell Mutant Carriers," *JAMA Neurol.*, 71(12): 1481-1489 (2014).
Mertens et al., "APP Processing in Human Pluripotent Stem Cell-Derived Neurons Is Resistant to NSAID-Based γ-Secretase Modulation," *Stem Cell Rep.*, 1(6): 491-498 (2013).

(Continued)

*Primary Examiner* — Theodore R. Howell
*Assistant Examiner* — George W Kosturko
(74) *Attorney, Agent, or Firm* — Leydig, Voit & Mayer, Ltd.

(57) ABSTRACT

The present invention provides a prophylactic or therapeutic agent for Alzheimer's disease (AD) containing a combination of two or more compounds selected from the group consisting of compounds shown by compound Nos. 1 to 130. Since these compounds are existing drugs that have already been confirmed actually for safety and pharmacokinetics in human, they can be a means for a pre-emptive treatment of people at risk of AD and in a stage before developing mild cognitive impairment (MCI).

4 Claims, 14 Drawing Sheets

(56) References Cited

OTHER PUBLICATIONS

Morley et al., "Metformin and Topiramate Improve Learning and Memory in Diabetic Mice and SAMP8 Mice Model of Alzheimer's Disease," *Alzheimer's and Dementia: Journal of the Alzheimer's Association*, 10(4): P477-P478, Abstract P2-021 (2014).

Sakurai et al., "Effects of cilostazol on cognition and regional cerebral blood flow in patients with Alzheimer's disease and cerebrovascular disease: A pilot study," *Geriatr. Gerontol. Int.*, 13(1): 90-97 (2013).

Santos et al., "Probucol Mitigates Streptozotocin-Induced Cognitive and Biochemical Changes in Mice," *Neuroscience*, 284: 590-600 (2015).

Shinohara et al., "Explanation of the Effects of Novel Fluvastatin Anti-Aβ for the Fundamental Treatment of Alzheimer's," *Japanese Journal of Geriatrics*, 46:52 (2009).

Yahata et al., "Anti-Aβ Drug Screening Platform Using Human iPS Cell-Derived Neurons for the Treatment of Alzheimer's Disease," *PLoS One*, 6(9): e25788 (2011).

Japanese Patent Office, International Preliminary Report in Patentability in International Patent Application No. PCT/JP2016/089217 (dated Jul. 3, 2018).

Japanese Patent Office, International Search Report in International Patent Application No. PCT/JP2016/089217 (dated Mar. 28, 2017).

Taguchi et al., "Cilostazol improves cognitive function in patients with mild cognitive impairment: a retrospective analysis," *Psychogeriatrics*, 13(3): 164-169 (2013).

Takechi et al., "Probucol prevents blood-brain barrier dysfunction in wild-type mice induced by saturated fat or cholesterol feeding," *Clin. Exp. Pharmacol. Physiol.*, 40(1): 45-52 (2013).

European Patent Office, Communication Pursuant to Rule 164(1) [Supplementary Partial European Search Report] in European Patent Application No. 16881847.4 (dated Aug. 1, 2019).

Kim et al., "Aβ40 Inhibits Amyloid Deposition In Vivo," *J. Neurosci.*, 27(3): 627-633 (2007).

Kumar-Singh et al., "Mean Age-of-Onset of Familial Alzheimer Disease Caused by Presenilin Mutations Correlates With Both Increased Aβ2 and Decreased Aβ0," *Human Mutation*, 27(7): 686-695 (2006).

\* cited by examiner

Fig. 1
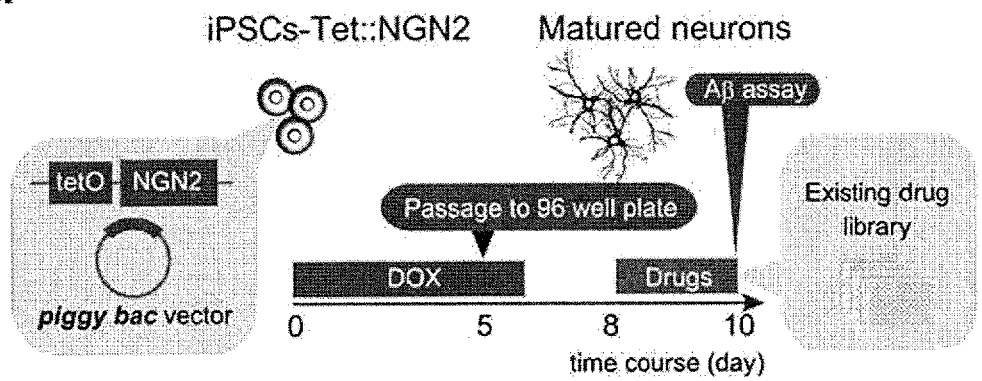
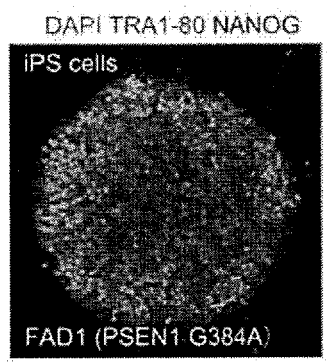
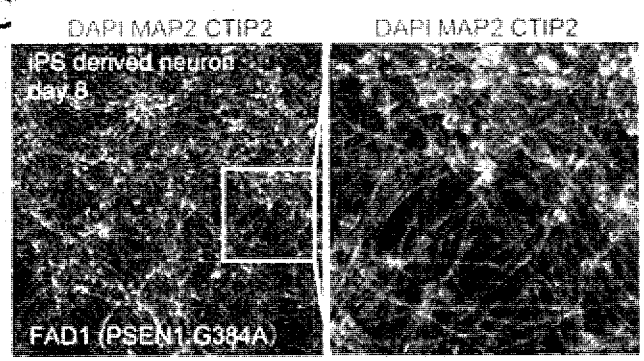
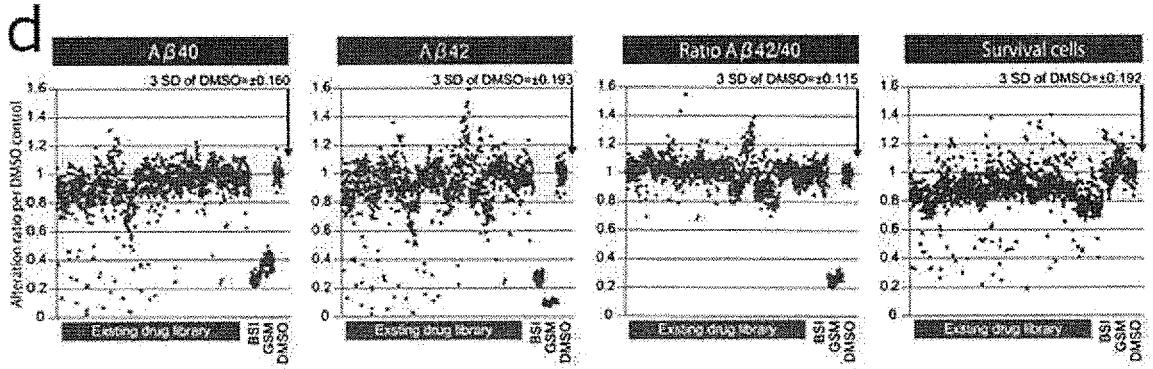
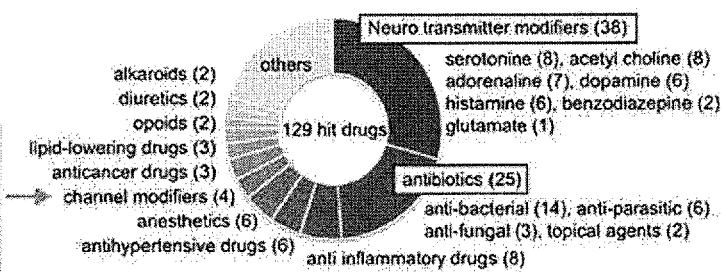

Fig. 2-1
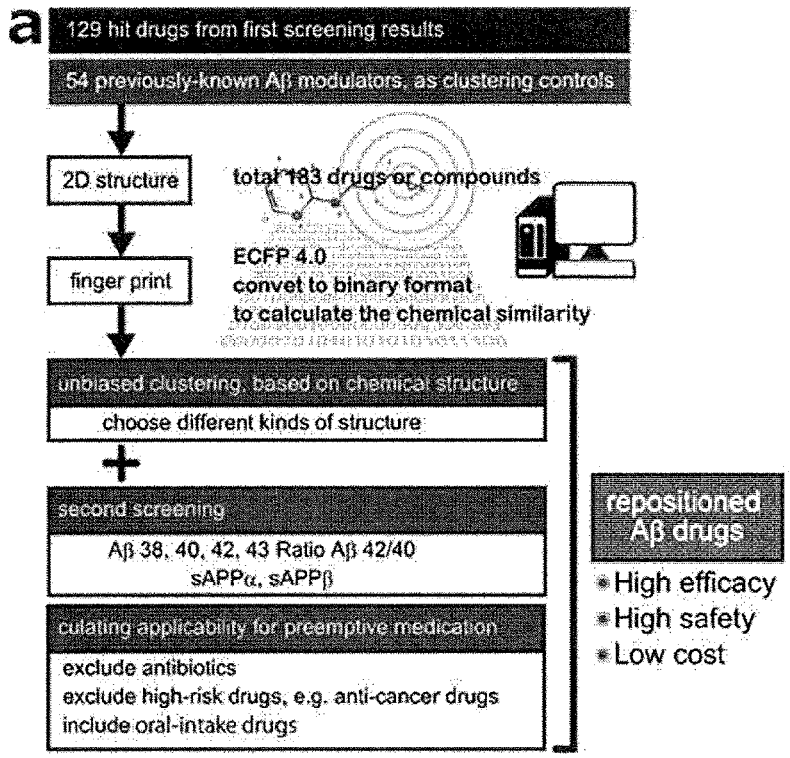
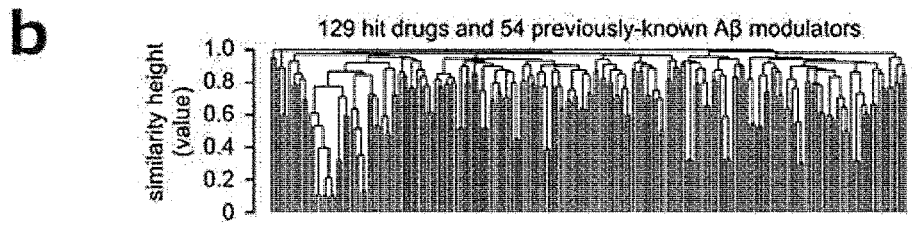
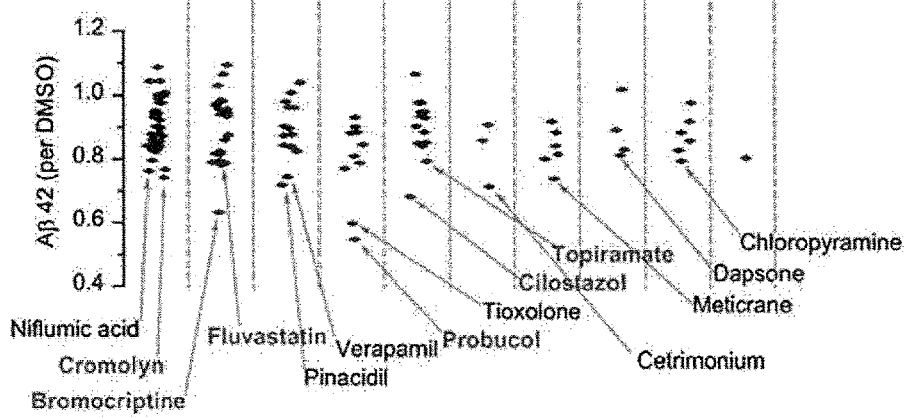

AGENT FOR PREVENTING AND/OR TREATING ALZHEIMER'S DISEASE

CROSS-REFERENCE TO RELATED APPLICATIONS

This patent application is the U.S. national phase of International Patent Application No. PCT/JP2016/089217, filed Dec. 29, 2016, which claims the benefit of Japanese Patent Application No. 2015-257706, filed on Dec. 29, 2015, which are incorporated by reference in their entireties herein.

TECHNICAL FIELD

The present invention relates to a prophylactic and/or therapeutic agent for Alzheimer's disease. More particularly, the present invention relates to a prophylactic and/or therapeutic agent for Alzheimer's disease, which is a combination of two or more compounds classified in different clusters and obtained by clustering, by molecular fingerprint, existing drugs showing improved amyloid β-pathology in nerve cells induced to differentiate from induced pluripotent stem cells (iPS cells) derived from patients with Alzheimer's disease.

BACKGROUND ART

Alzheimer's disease (AD) is a type of dementia with main symptoms of decline in cognitive function and change of personality. AD brain lesions are characterized by degeneration and disappearance of nerve cells and cerebral atrophy associated therewith, frequent occurrence of senile plaques, and frequent occurrence of neurofibrillary tangles (NFT). Of these, senile plaques are known to be aggregation and accumulation of amyloid β (Aβ) peptide. Aβ is a peptide consisting of 38-43 amino acids produced as a result of cleavage of amyloid precursor protein (APP) by β- and γ-secretases. Of these, Aβ42 is known to have high aggregation activity and toxicity against nerve cells, and it has been reported that an increase in Aβ 42/40 ratio is observed in cells having causative mutation for familial Alzheimer's disease (FAD).

Conventionally, it is widely recognized that decreasing the amount of Aβ42 becomes a key point for suppressing the onset of AD. This is clear also from the fact that some of the modulator drugs of β- or γ-secretase have been shown to reduce the onset of AD in a mouse model overexpressing presenilin 1 (PSEN1) or mutant APP.

Despite significant success in preclinical tests using AD model mice, these modulator drugs failed in many clinical tests when used for human.

From the results of antibody therapy, it has heretofore been shown that lesions caused by accumulation of Aβ, including senile plaques, are reversible. Unfortunately, however, clinical effectiveness has not been obtained even when Aβ accumulation was eliminated, and intervention at a stage before developing mild cognitive impairment (MCI) is considered to be necessary. Amyloid PET (positron emission tomography) has also demonstrated that the pathological change of Aβ already precedes in the stage before developing MCI, and intervention in the pre-symptomatic stage is necessary for people at risk of AD and predicted to be present in a large number. In particular, the importance of preventive therapy including dominantly inherited Alzheimer network (DIAN) research is emphasized. However, aggressive application of very expensive antibody medicines to such subjects is not realistic. In addition, treatments by oral administration of many compounds targeting Aβ have also been tried, but none of them have been placed on the market due to the problems of side effects.

Therefore, solutions of drug safety and pre-emptive treatment (early treatment) are considered essential for making drugs targeting Aβ effective.

On the other hand, a rapid increase in AD patients associated with the advancement of aging society is putting pressure on the medical economy. As of 2010, the medical expenses for 35 million AD patients are $ 604 billion per year. AD patients are expected to increase to 114 million in 2050 and the medical expenses are predicted to rise further. Under these circumstances, importance is placed on drug repositioning (DR) for AD treatment, that is, diverted application of existing drugs (non-patent document 1). Enormous clinical information relating to safety and pharmacokinetics of existing drugs has already been accumulated (Chembl database and the like) and the safety has already been established. Thus, intervention as a pre-emptive treatment for people at risk of AD who do not have clinical symptoms but have been judged positive by amyloid test can be expected. In fact, Valsartan (depressor) and Liraglutide (antidiabetic drug) have proceeded to clinical trial. As described above, the importance of DR in the AD treatment is predicted to further increase in the future.

Incidentally, a cell causing the disease that was induced to differentiate from patient-derived iPS cells (disease iPS cells) is assumed to reproduce pathology of the patient in vitro. Accordingly, it is expected as a promising system for efficacy evaluation. In recent reports relating to nerve cells derived from human iPS cells, the importance of human nerve cell as a tool for evaluating drug responsiveness is stressed (non-patent documents 2-4).

DOCUMENT LIST

Non-Patent Documents non-patent document 1: Front. Biosci. (Schol. Ed). 7,184-8 (2015)
non-patent document 2: PLoS One 6, e25788 (2011)
non-patent document 3: JAMA Neurol. 71, 1481-9 (2014)
non-patent document 4: Stem Cell Reports 1,491-498 (2013)

SUMMARY OF THE INVENTION

Problems to be Solved by the Invention

An object of the present invention is to find drugs having a prophylactic and/or therapeutic effect on Alzheimer's disease from existing drugs that have already been confirmed actually for safety and pharmacokinetics in human, thereby providing a means for a pre-emptive treatment of people at risk of AD and in a stage before developing MCI.

Means of Solving the Problems

In an attempt to achieve the aforementioned object, the present inventors have screened an existing drug library consisting of 1280 kinds of pharmaceutical compounds approved by the Food and Drug Administration (FDA) in America by using nerve cells induced to differentiate from iPS cells derived from AD patients, and extracted 129 kinds (including one kind of concomitant drug) of compounds that improve Aβ pathology in the nerve cells as candidate therapeutic drugs for AD. Furthermore, they have classified these candidate compounds in 10 cluster compounds based on the structure and property, and found a combination of clusters that acts additively as compared to a single agent. The present inventors have conducted further studies based on these findings and completed the present invention.

That is, the present invention provides the following.

[1] A prophylactic or therapeutic agent for Alzheimer's disease comprising a combination of two or more compounds selected from the group consisting of compounds shown by compound Nos. 1 to 130.
[2] The agent of [1], wherein the combined two or more kinds of compounds belong to two or more clusters selected from the group consisting of clusters 1, 2, 4 and 5.
[3] The agent of [2], wherein the compound belonging to the cluster 1 is Cromolyn, the compound belonging to the cluster 2 is Bromocriptine and/or Fluvastatin, the compound belonging to the cluster 4 is Probucol, and the compound belonging to the cluster 5 is Cilostazol and/or Topiramate.
[4] The agent of any of [1] to [3], wherein the combined two or more compounds are selected from the group consisting of Bromocriptine, Cilostazol, Cromolyn, Fluvastatin, Probucol and Topiramate.
[5] The agent of [4], wherein Bromocriptine, Cromolyn and Topiramate are combined.
[6] The agent of [4], wherein Bromocriptine, Cilostazol and Probucol are combined.
[7] A method for preventing or treating Alzheimer's disease in a subject, comprising administering to the subject a therapeutically effective amount of each of the two or more compounds selected from the group consisting of compounds shown by compound Nos. 1 to 130.
[8] The method of [7], wherein the aforementioned therapeutically effective amount is not more than a known maximum nontoxic dose of each compound.

Effect of the Invention

According to the present invention, it is possible to prevent and/or treat Alzheimer's disease for which an effective prophylactic or therapeutic drug does not exist. Particularly, existing drugs confirmed to be safe are used as active ingredients in the present invention, the fear of side effects is less and an aggressive pre-emptive treatment can be performed on people at risk of AD and in a stage before developing MCI.

BRIEF DESCRIPTION OF THE DRAWINGS

FIG. 1 FIG. 1a is a schematic showing of the induction method of iPS cell into cortical neurone. FIG. 1b shows the results of staining of iPS cells prepared from FAD1 patient for Tra-1-80 and Nanog. FIG. 1c shows an image of neurons induced from iPS cells prepared from FAD1 patient, which were stained for MAP2 and CTIP2. The right figure is an enlarged figure of the left figure. FIG. 1d shows the results plotted for each index (Aβ40, Aβ42, Aβ42/Aβ40 ratio and viable cell number) in the primary screen. FIG. 1e shows a sorting method of the primary screening and classification of 129 candidate drugs.

FIG. 2-2 FIG. 2a shows the reclassification strategy and study items based on the compound structure and not relying on known efficacy. FIG. 2b shows the results of clustering classification of 129 candidate drugs and known Aβ modulation compounds based on the structural formulas, and efficacy plot on Aβ42 afforded by the classified candidate drugs.

FIG. 2-2 FIG. 2c shows dose dependency of Bromocriptine, Cilostazol, Cromolyn, Fluvastatin, Probucol and Topiramate with Aβ40, Aβ42, Aβ42/Aβ40 ratio as indices.

FIG. 3-1 FIG. 3a shows dose dependency of Bromocriptine, Cromolyn and Topiramate (BCroT) or Bromocriptine, Cilostazol and Probucol (BCiP) with Aβ40, Aβ42, Aβ42/Aβ40 ratio as indices. FIG. 3b shows dose dependency of combined use of Donepezil and BCroT or BCiP with Aβ40, Aβ42, Aβ42/Aβ40 ratio as indices. FIG. 3c shows the results of EC50 and Emax of Aβ40, Aβ42, Aβ42/Aβ40 ratio by Bromocriptine, Cilostazol, Cromolyn, Fluvastatin, Probucol, Topiramate, BCroT, BCiP, combined use of Donepezil and BCroT and combined use of Donepezil and BCiP. FIG. 3d shows the efficacy reevaluation process of existing drugs based on human iPS cells and a conceptual diagram of an "in vitro clinical test" using nerve cells derived from human iPS cells derived from a large number of people. FIG. 3e shows a list of patients and healthy individuals used in in vitro clinical test.

FIG. 3-2 FIG. 3f shows effects of Bromocriptine, Cilostazol, Cromolyn, Fluvastatin, Probucol, Topiramate, BCroT, BCiP on Aβ40, Aβ42, Aβ42/Aβ40 ratio in each neuron derived from iPS cell shown in FIG. 3e.

FIG. 3-3 FIGS. 3g and h show effects on intracerebral Aβ afforded by oral administration of BCroT and BCiP to ICR mouse.

FIG. 4 FIG. 4a shows the results of staining of each iPS cell for Tra-1-80 and Nanog. FIG. 4b shows images of neurons induced from each iPS cell, which were stained for MAP2 and CTIP2. FIG. 4c shows positive ratio of neural markers (MAP2 and CTIP2) in neuron induced from each iPS cell. FIG. 4d shows the differentiation induction protocol of iPS cells (FAD1) and the study results of time-course changes in the expression of an endogenous neural marker gene and exogeneous gene. FIG. 4e shows electrophysiological test results in neuron derived from iPS cell (FAD1). FIG. 4f shows measurement results of time-course changes in Aβ40, Aβ42 and Aβ42/Aβ40 ratio produced by each neuron derived from iPS cell.

FIG. 5 FIG. 5a shows measurement results of efficacy of compounds having a known action of Aβ amount regulation, FIG. 5b shows those of previously-reported γ-secretase modulators, FIG. 5c shows those of commercially available therapeutic drugs for AD, respectively on neuron derived from iPS cell of FAD1 patient.

FIG. 6 FIG. 6a shows dose dependency when BSI IV and JNJ-40418677 used as a positive control was administered to neuron derived from iPS cell (FAD1) with Aβ40, Aβ42, Aβ42/Aβ40 ratio as indices. FIG. 6b shows Z' factor in the primary screening method with Aβ40, Aβ42, Aβ42/Aβ40 ratio as indices. FIG. 6c shows Venn diagram of drugs effective for Aβ40, Aβ42 or Aβ42/Aβ40 ratio from 129 drugs selected by primary screening.

FIG. 7 FIG. 7a, b, c, d, e, f and g respectively show effects on Aβ40, Aβ42, ratio Aβ42/40, Aβ38, sAPPbeta, sAPPalpha or Aβ43 of each cluster.

FIG. 10 FIG. 10a shows the study results of effects of Dopamin, DA agonist (SKF38393, Bromocriptine and PD168077) on Aβ40, Aβ42 or Aβ42/Aβ40 in neuron derived from iPS cell (FAD1). FIG. 10*b* shows the study results of effects of Talipexole, Pramipexole, Ropinirole and Cabergoline on Aβ40, Aβ42 or Aβ42/Aβ40 in neuron derived from iPS cell (FAD1).

DESCRIPTION OF EMBODIMENTS

Figure 2:
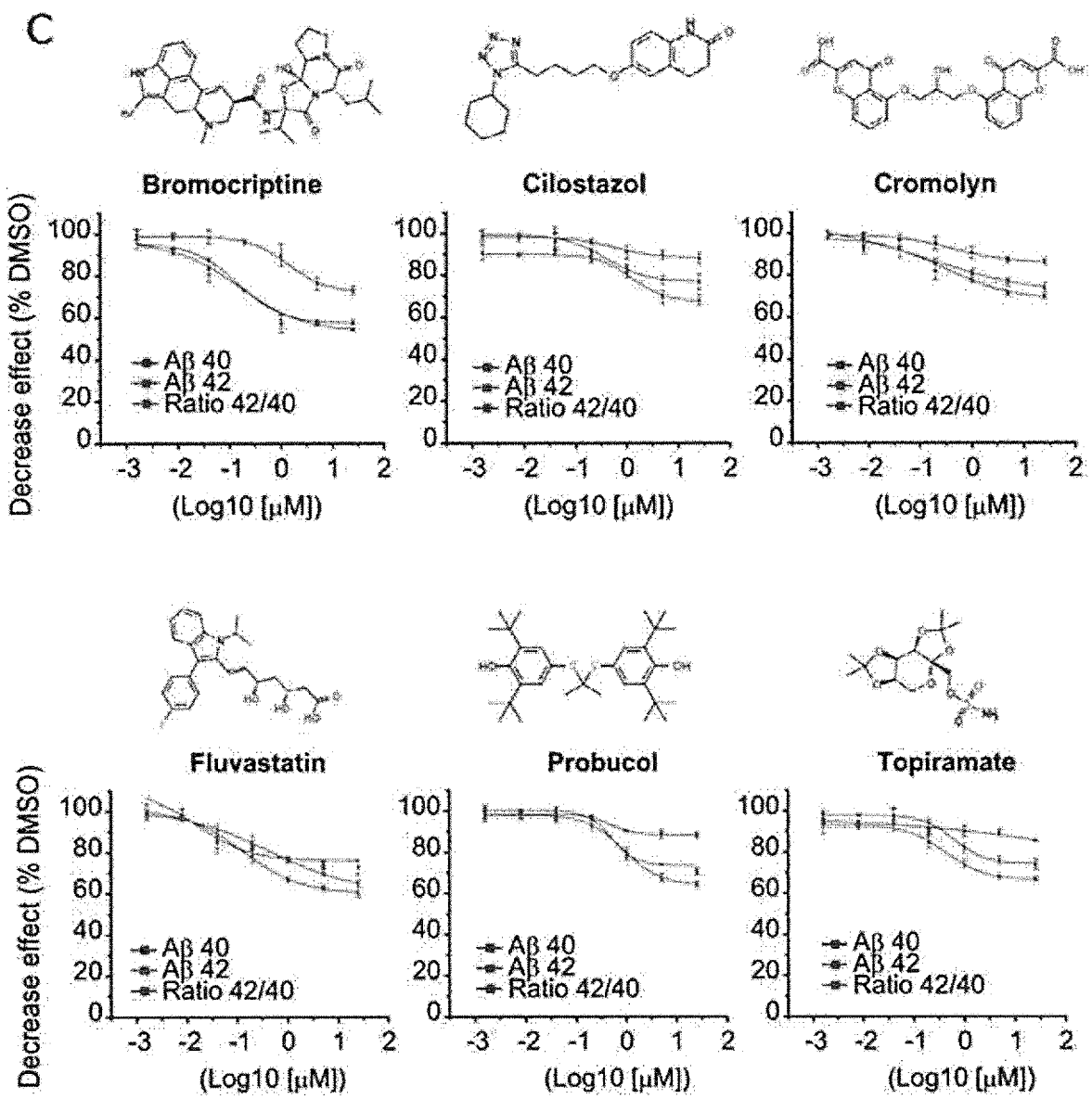

The present invention is explained in the following. The terms used in the present specification have the meanings generally used in the pertinent field unless otherwise specified.

The present invention provides a prophylactic and/or therapeutic agent for Alzheimer's disease (hereinafter to be also referred to as "the medicament of the present invention") composed of a combination of two or more compounds each capable of improving Aβ pathology in human nerve cell showing the pathology of Alzheimer's disease (hereinafter to be also referred to as "AD nerve cell") and affording an additive Aβ pathology improving effect in combination as compared to use thereof as single agents.

Specifically, the medicament of the present invention comprises two or more compounds selected from the group consisting of compound Nos. 1 to 130 described in the following Tables 1-1 to 1-19 as active ingredients.

TABLE 1-1

| comp. No. | structural formula | name | cluster |
|---|---|---|---|
| 1 | | OXYPHENCYCLIMINE (marketing drug is hydrochloride) | 1 |
| 2 | | MEPIVACAINE (marketing drug is hydrochloride) | 1 |
| 3 | | RANOLAZINE | 1 |
| 4 | | ATOMOXETINE (marketing drug is hydrochloride) | 1 |
| 5 | | TERBINAFINE (marketing drug is hydrochloride) | 1 |

TABLE 1-1-continued

| comp. No. | structural formula | name | cluster |
|---|---|---|---|
| 6 | | LOPERAMIDE (marketing drug is hydrochloride) | 1 |
| 7 | | ALVERINE (marketing drug is citrate) | 1 |

TABLE 1-2

| comp. No. | structural formula | name | cluster |
|---|---|---|---|
| 8 | | APOMORPHINE (marketing drug is hydrochloride) | 1 |
| 9 | | CLOMIPHENE (marketing drug is citrate) | 1 |
| 10 | | COTININE | 1 |
| 11 | | CROMOLYN (marketing drug is sodium salt) | 1 |

TABLE 1-2-continued

| comp. No. | structural formula | name | cluster |
|---|---|---|---|
| 12 | | CYCLIZINE | 1 |
| 13 | | DESIPRAMINE (marketing drug is hydrochloride) | 1 |
| 14 | | diphenhydramine (combination agent with 8-chlorotheophylline) | 1 |

TABLE 1-3

| comp. No. | structural formula | name | cluster |
|---|---|---|---|
| 15 | | ETHOPROPAZINE (marketing drug is hydrochloride) | 1 |
| 16 | | HOMATROPINE (marketing drug is bromide) | 1 |
| 17 | | IMIPRAMINE (marketing drug is hydrochloride) | 1 |

TABLE 1-3-continued

| comp. No. | structural formula | name | cluster |
|---|---|---|---|
| 18 | | TACRINE (marketing drug is hydrochloride) | 1 |
| 19 | | ISOPROPAMIDE (marketing drug is iodide) | 1 |
| 20 | | THIABENDAZOLE | 1 |
| 21 | | BETAHISTINE (marketing drug is hydrochloride) | 1 |

TABLE 1-4

| comp. No. | structural formula | name | cluster |
|---|---|---|---|
| 22 | | VESAMICOL (marketing drug is hydrochloride) | 1 |
| 23 | | MONOBENZONE | 1 |
| 24 | | CINCHONINE | 1 |
| 25 | | LOXAPINE (marketing drug is succinate) | 1 |

TABLE 1-4-continued

| comp. No. | structural formula | name | cluster |
|---|---|---|---|
| 26 | | ETODOLAC | 1 |
| 27 | | BIFONAZOLE | 1 |
| 28 | | NOMIFENSINE (marketing drug is maleate) | 1 |

TABLE 1-5

| comp. No | structural formula | name | cluster |
|---|---|---|---|
| 29 | | CARBADOX | 1 |
| 30 | | LEVOCETIRIZINE (marketing drug is dihydrochloride) | 1 |
| 31 | | METITEPINE (marketing drug is maleate) | 1 |

TABLE 1-5-continued

| comp. No | structural formula | name | cluster |
| --- | --- | --- | --- |
| 32 | | BETAMIPRON | 1 |
| 33 | | CAMYLOFINE (marketing drug is dihydrochloride) | 1 |
| 34 | | NIALAMIDE | 1 |
| 35 | | CHINIOFON | 1 |

TABLE 1-6

| comp. No. | structural formula | name | cluster |
| --- | --- | --- | --- |
| 36 | | PIRIBEDIL (marketing drug is hydrochloride) | 1 |
| 37 | | NIFLUMIC ACID | 1 |

TABLE 1-6-continued

| comp. No. | structural formula | name | cluster |
|---|---|---|---|
| 38 | | CYPERMETHRIN | 1 |
| 39 | | NAFTOPIDIL | 1 |
| 40 | | CYCLANDELATE | 1 |
| 41 | | QUININE ETHYL CARBONATE | 1 |
| 42 | | PIPENZOLATE (marketing drug is bromide) | 1 |

TABLE 1-7

| comp. No | structural formula | name | cluster |
|---|---|---|---|
| 43 | | IDAZOXAN (marketing drug is hydrochloride) | 1 |
| 44 | | IFENPRODIL (marketing drug is tartrate) | 1 |

TABLE 1-7-continued

| comp. No | structural formula | name | cluster |
|---|---|---|---|
| 45 | | EBSELEN | 1 |
| 46 | | LOVASTATIN | 2 |
| 47 | | AMINOLEVULINIC ACID (marketing drug is hydrochloride) | 2 |
| 48 | | VALSARTAN | 2 |
| 49 | | AMINOCAPROIC ACID | 2 |

TABLE 1-8

| comp. No. | structural formula | name | cluster |
|---|---|---|---|
| 50 | | AMINOSALICYLATE (marketing drug is sodium salt) | 2 |
| 51 | | BENZOCAINE | 2 |

TABLE 1-8-continued
| comp. No. | structural formula | name | cluster |
|---|---|---|---|
| 52 | 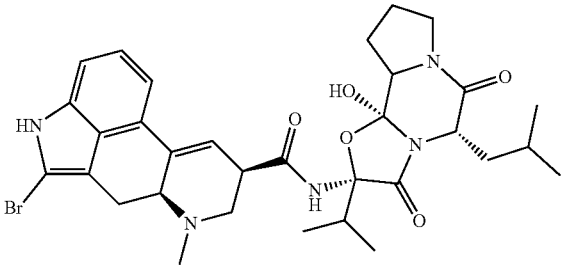 [SMILES: CC(C)C[C@H]1C(=O)N2CCCC2[C@]2(O)O[C@](NC(=O)[C@@H]3C=C4c5cccc6[nH]c(Br)c(c56)C[C@@H]4N(C)C3)(C(C)C)C(=O)N12] | BROMOCRIPTINE (marketing drug is mesylate) | 2 |
| 53 | 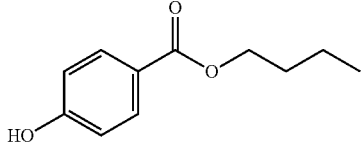 | BUTYL PARABEN | 2 |
| 54 | 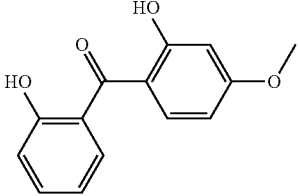 [SMILES: COc1ccc(C(=O)c2ccccc2O)c(O)c1] | DIOXYBENZONE | 2 |
| 55 | 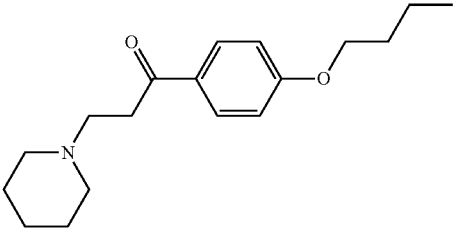 [SMILES: CCCCOc1ccc(C(=O)CCN2CCCCC2)cc1] | DYCLONINE (marketing drug is hydrochloride) | 2 |
| 56 | 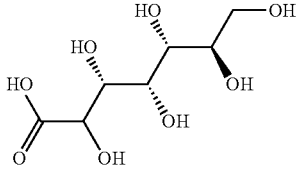 | GLUCOHEPTONIC ACID (marketing drug is calcium salt) | 2 |
TABLE 1-9
| comp. No | structural formula | name | cluster |
|---|---|---|---|
| 57 | 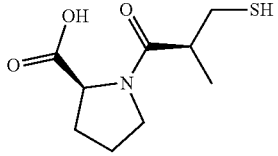 | CAPTOPRIL | 2 |
| 58 | 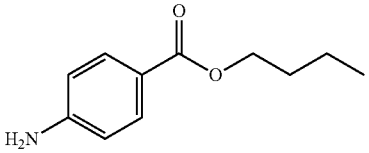 | BUTAMBEN | 2 |

TABLE 1-9-continued

| comp. No | structural formula | name | cluster |
|---|---|---|---|
| 59 | | BACAMPICILLIN (marketing drug is hydrochloride) | 2 |
| 60 | | FLUVASTATIN | 2 |
| 61 | | OLMESARTAN MEDOXOMIL | 2 |
| 62 | | CEFTIBUTEN | 2 |
| 63 | | CEFDINIR | 2 |

TABLE 1-10

| comp. No. | structural formula | name | cluster |
|---|---|---|---|
| 64 | | PERINDOPRIL ERBUMINE | 2 |
| 65 | | ZOMEPIRAC (marketing drug is sodium salt) | 2 |
| 66 | | CEFAMANDOLE | 2 |
| 67 | | HYDROXYTOLUIC ACID | 2 |
| 68 | | DIACETAMATE | 2 |
| 69 | | PIROMIDIC ACID | 2 |
| 70 | | BUCETIN | 2 |

TABLE 1-11

| comp. No. | structural formula | name | cluster |
|---|---|---|---|
| 71 | | REBAMIPIDE | 2 |
| 72 | | HYDROXYCHLOROQUINE (marketing drug is sulfate) | 3 |
| 73 | | LEVALBUTEROL (marketing drug is hydrochloride) | 3 |
| 74 | | PINACIDIL | 3 |
| 75 | | VERAPAMIL (marketing drug is hydrochloride) | 3 |
| 76 | | DIBUCAINE (marketing drug is hydrochloride | 3 |

TABLE 1-11-continued
| comp. No. | structural formula | name | cluster |
|---|---|---|---|
| 77 | 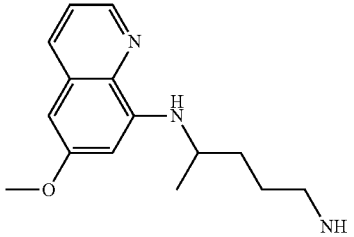 [SMILES: COc1cc(NC(C)CCCN)c2ncccc2c1] | PRIMAQUINE (marketing drug is diphosphate) | 3 |
TABLE 1-12
| comp. No | structural formula | name | cluster |
|---|---|---|---|
| 78 | 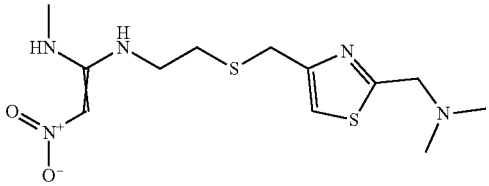 [SMILES: CNC(=C[N+](=O)[O-])NCCSCc1csc(CN(C)C)n1] | NIZATIDINE | 3 |
| 79 | 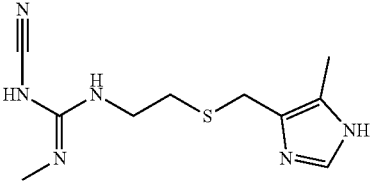 [SMILES: C/N=C(\NC#N)NCCSCc1nc[nH]c1C] | CIMETIDINE | 3 |
| 80 | 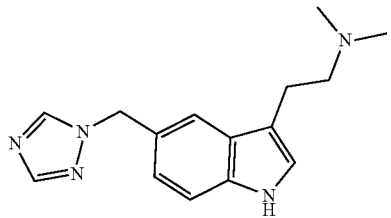 [SMILES: CN(C)CCc1c[nH]c2ccc(Cn3cncn3)cc12] | RIZATRIPTAN (marketing drug is benzoate) | 3 |
| 81 | 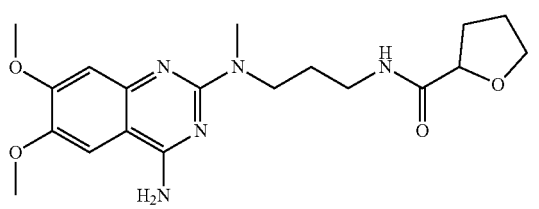 [SMILES: COc1cc2nc(N(C)CCCNC(=O)C3CCCO3)nc(N)c2cc1OC] | ALFLUZOSIN | 3 |
| 82 | 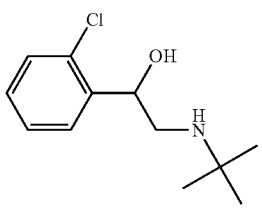 | TULOBUTEROL | 3 |

TABLE 1-12-continued
| comp. No | structural formula | name | cluster |
|---|---|---|---|
| 83 | 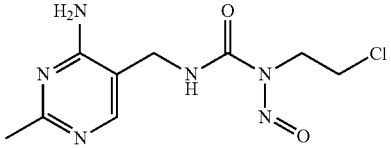 [SMILES: Cc1ncc(CNC(=O)N(CCCl)N=O)c(N)n1] | NIMUSTINE | 3 |
| 84 | 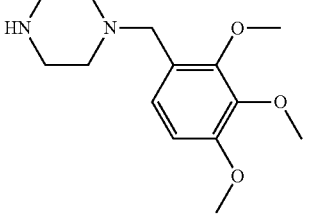 | TRIMETAZIDINE (marketing drug is dihydrochloride) | 3 |
TABLE 1-13
| comp. No | structural formula | name | cluster |
|---|---|---|---|
| 85 | 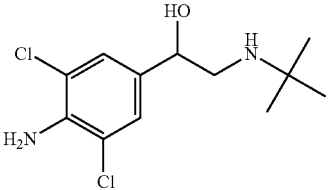 [SMILES: CC(C)(C)NCC(O)c1cc(Cl)c(N)c(Cl)c1] | CLENBUTEROL (marketing drug is hydrochloride) | 3 |
| 86 | 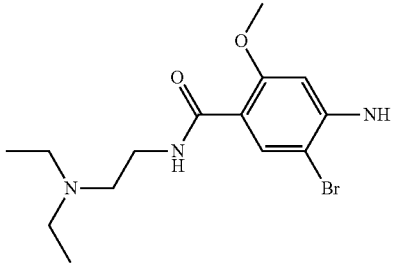 [SMILES: CCN(CC)CCNC(=O)c1cc(Br)c(N)cc1OC] | BROMOPRIDE | 3 |
| 87 | 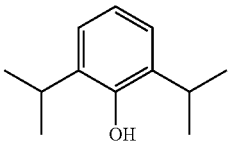 | PROPOFOL | 4 |
| 88 | 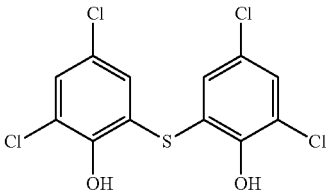 [SMILES: Oc1c(Cl)cc(Cl)cc1Sc1cc(Cl)cc(Cl)c1O] | BITHIONOL (marketing drug is sodium salt) | 4 |
| 89 | 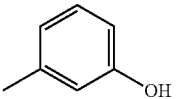 | CRESOL | 4 |

TABLE 1-13-continued

| comp. No | structural formula | name | cluster |
|---|---|---|---|
| 90 | | DOPAMINE (marketing drug is hydrochloride) | 4 |
| 91 | | TRIOXSALEN | 4 |

TABLE 1-14

| comp. No | structural formula | name | cluster |
|---|---|---|---|
| 92 | | TIOXOLONE | 4 |
| 93 | | METACETAMOL | 4 |
| 94 | | DICHLOROPHENE | 4 |
| 95 | | DINITOLMIDE | 4 |
| 96 | | PROBUCOL | 4 |

TABLE 1-14-continued
| comp. No | structural formula | name | cluster |
|---|---|---|---|
| 97 | 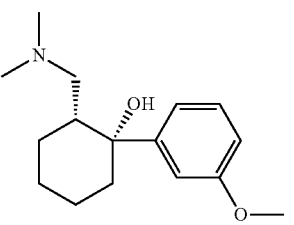 | RIFAXIMIN | 5 |
| 98 | 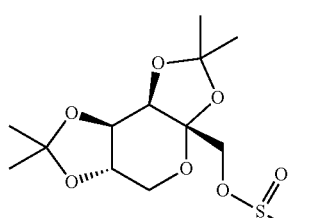 | DESOXYCORTICOSTERONE (marketing drug is acetate) | 5 |
TABLE 1-15
| comp. No | structural formula | name | cluster |
|---|---|---|---|
| 99 | 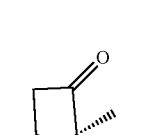 | TRAMADOL (marketing drug is hydrochloride) | 5 |
| 100 | | TOPIRAMATE | 5 |
| 101 | | CAMPHOR (1R) | 5 |

TABLE 1-15-continued
| comp. No | structural formula | name | cluster |
|---|---|---|---|
| 102 | 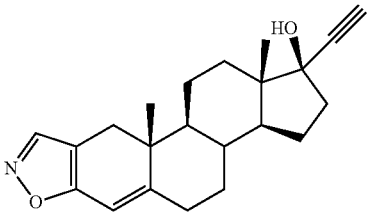 | DANAZOL | 5 |
| 103 | 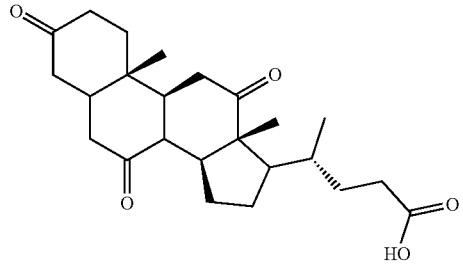 | DEHYDROCHOLIC ACID (marketing drug is sodium salt) | 5 |
| 104 | 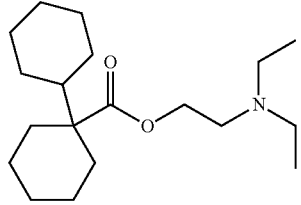 [SMILES: CCN(CC)CCOC(=O)C1(C2CCCCC2)CCCCC1] | DICYCLOMINE (marketing drug is hydrochloride) | 5 |
| 105 | 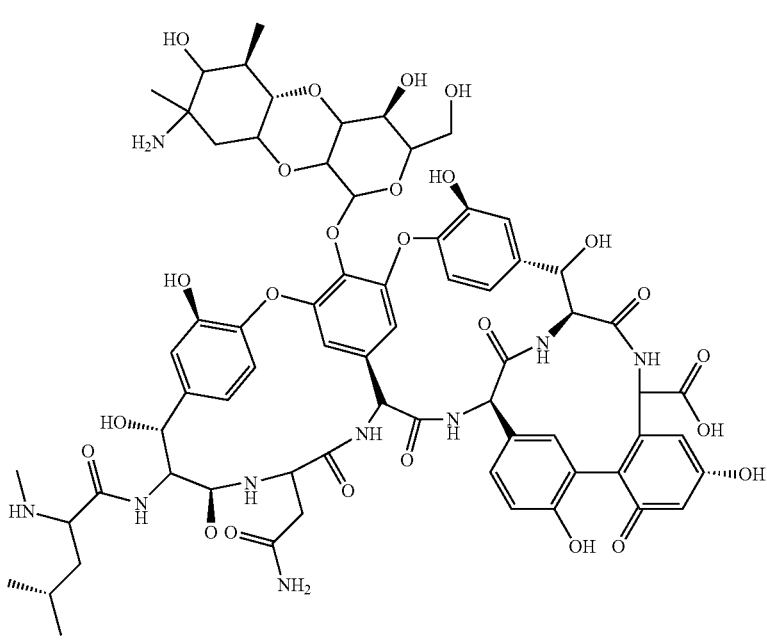 | VANCOMYCIN (marketing drug is hydrochloride) | 5 |

TABLE 1-16
| comp. No. | structural formula | name | cluster |
|---|---|---|---|
| 106 | 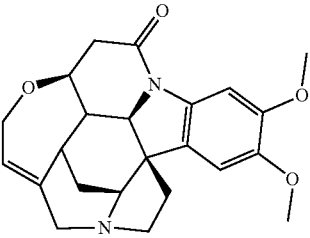 | BRUCINE | 5 |
| 107 | 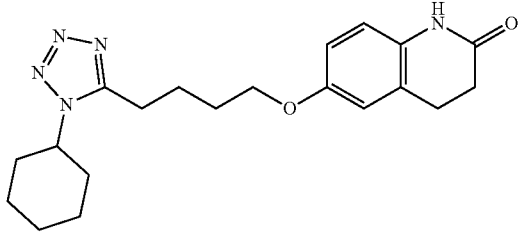 [SMILES: O=C1CCc2cc(OCCCCc3nnnn3C3CCCCC3)ccc2N1] | CILOSTAZOL | 5 |
| 108 | 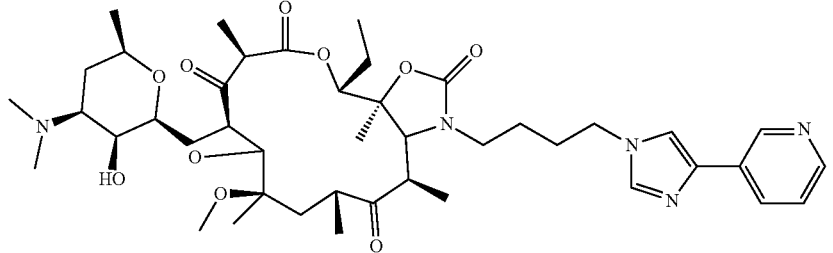 [SMILES: CC[C@H]1OC(=O)[C@H](C)C(=O)[C@H](C[C@@H]2O[C@H](C)C[C@H](N(C)C)[C@@H]2O)C(O)[C@](C)(OC)C[C@@H](C)C(=O)[C@H](C)C2N(CCCCn3cnc(-c4cccnc4)c3)C(=O)O[C@@]21C] | TELITHROMYCIN | 5 |
| 109 | 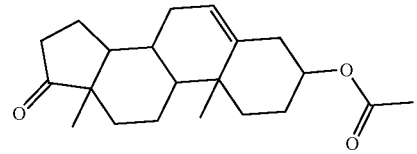 [SMILES: CC(=O)OC1CCC2(C)C(=CCC3C4CCC(=O)C4(C)CCC32)C1] | PRASTERONE ACETATE | 5 |
| 110 | 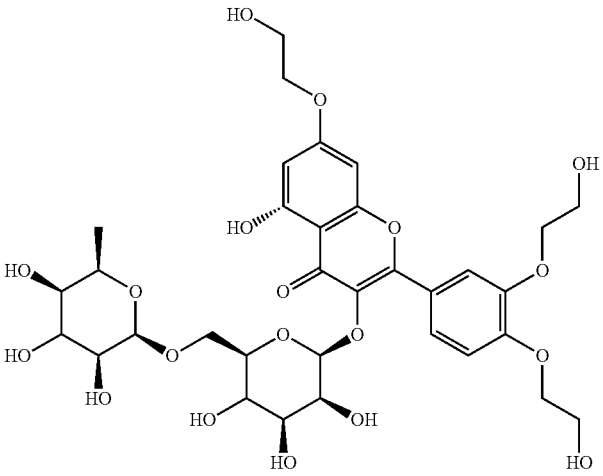 | TROXERUTIN | 5 |
| 111 | 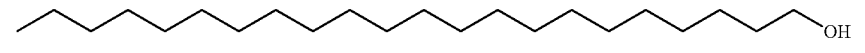 [SMILES: CCCCCCCCCCCCCCCCCCCCCCO] | DOCOSANOL | 6 |

TABLE 1-16-continued

| comp. No. | structural formula | name | cluster |
|---|---|---|---|
| 112 | | DISULFIRAM | 6 |

TABLE 1-17

| comp. No. | structural formula | name | cluster |
|---|---|---|---|
| 113 | | CETRIMONIUM (marketing drug is bromide) | 6 |
| 114 | | CYCLOSERINE | 7 |
| 115 | | CYTARABINE | 7 |
| 116 | | ALLANTOIN | 7 |
| 117 | | ALTHIAZIDE | 7 |
| 118 | | CLAVULANIC ACID (marketing drug is lithium salt) | 7 |
| 119 | | METICRANE | 7 |

TABLE 1-18

| comp. No | structural formula | name | cluster |
|---|---|---|---|
| 120 | | DAPSONE | 8 |
| 121 | | HISTAMINE (marketing drug is dihydrochloride) | 8 |
| 122 | | THIOGUANINE | 8 |
| 123 | | BITOSCANATE | 8 |
| 124 | | 8-chlorotheophylline (combination agent with diphenhydramine) | 9 |
| 125 | | DIAZOXIDE | 9 |
| 126 | | SIBUTRAMINE (marketing drug is hydrochloride) | 9 |

TABLE 1-19

| comp. No | structural formula | name | cluster |
|---|---|---|---|
| 127 | | CHLORINDIONE | 9 |
| 128 | | CHLORMEZANONE | 9 |

TABLE 1-19-continued

| comp. No | structural formula | name | cluster |
|---|---|---|---|
| 129 | | CHLOROPYRAMINE (marketing drug is hydrochloride) | 9 |
| 130 | | FLUROTHYL | 10 |

As the compound of the present invention, a commercially available product may be used, or each compound can be produced by each method known per se. For example, a commercial source of each compound in the US can be known from Drugs@FDA (http://www.accessdata.fda.gov/scripts/cder/drugsatfda/index.cfm) and the like.

Each compound Table 1 described in encompasses not only a free form but also a pharmacologically acceptable salt thereof. While the pharmacologically acceptable salt varies depending on the kind of the compound, examples thereof include base addition salts such as salts with inorganic base such as alkali metal salts (sodium salt, potassium salt etc.), alkaline earth metal salts (calcium salt, magnesium salt etc.), aluminum salt, ammonium salt and the like, and salts with organic base such as trimethylamine, triethylamine, pyridine, picoline, ethanolamine, diethanolamine, triethanolamine, dicyclohexylamine, N,N'-dibenzylethylenediamine and the like and the like, and acid addition salts such as salts with inorganic acid such as hydrochloride, hydrobromide, sulfate, hydroiodide, nitrate salt, phosphate and the like, and salts with organic acid such as citrate, oxalate, acetate, formate, propionate, benzoate, trifluoroacetate, maleate, tartrate, methanesulfonate, benzenesulfonate, para-toluenesulfonate and the like, and the like.

In addition, each compound described in Table 1 may also be a halide (fluoride, chloride, bromide, iodide etc.).

When any one of compounds described in Table 1 contains isomers such as an optical isomer, a stereoisomer, a regioisomer or a rotamer, any one of the isomers and mixtures are also encompassed in the compound. For example, when any one of compounds described in Table 1 contains an optical isomer, an optical isomer resolved from racemate is also encompassed in the compound. These isomers can be obtained as single products by a synthesis method, a separation method (e.g., concentration, solvent extraction, column chromatography, recrystallization etc.), an optical resolution method (e.g., fractional recrystallization, chiral column method, diastereomer method etc.) and the like each known per se.

Each compound described in Table 1 may be a crystal, and is included in the compound of the present invention whether it is in a single crystal form or a crystal mixture. The crystal can be produced by crystallizing by applying a crystallization method known per se.

Each compound described in Table 1 may be a solvate (e.g., hydrate etc.) or a non-solvate (e.g., non-hydrate etc.), both of which are encompassed in the compound of the present invention.

In addition, a compound labeled with an isotope (e.g., $^3$H, $^{14}$C, $^{35}$S, $^{125}$I etc.) etc. is also encompassed in the compound described in Table 1.

Each compound described in Table 1 is a pharmaceutical compound approved by FDA for application other than AD (see FIG. 1e) (compound Nos. 14 and 124 were approved as concomitant drug (DIMENHYDRINATE)). In the below-mentioned Examples, these compounds were demonstrated to have one or more actions to improve pathological changes of Aβ in AD nerve cells (i.e., (1) decrease in Aβ42 level, (2) decrease in Aβ40 level, (3) decrease in Aβ42/40 ratio) (Table 2, FIG. 1e, FIG. 6c). These compound may have an action to change one or more of the level of other Aβ peptide species (Aβ38, Aβ43) and the level of soluble APP (sAPP-α, sAPP-β) obtained by cleavage by α- or β-secretase toward the direction improving AD pathology.

Each compound described in Table 1 is classified in 10 clusters by converting the molecular structure thereof to fingerpprinting information by using Extended Connectivity Fingerprint (ECFP) method (Rogers D et al. J Chem Inf Model. 2010 24; 50(5):742-54.) and performing clustering analysis based on the distance matrix (FIG. 2a) (Table 1, FIG. 2b). That is, compounds belonging to the same cluster form a compound group having similarity depending on the structural formula and not biased by known efficacy.

Using two or more compounds having different medicament structures in combination, simultaneous action can be performed on plural treatment targets. As a result, a superior treatment effect (e.g., additive effect, preferably a synergistic effect) is exhibited as compared to single administration of individual compounds. That "a superior effect is exhibited as compared to single administration of individual compounds" means that the maximum effect value (Emax) or 50% effect concentration (EC50) is superior to that by single administration or the kind of pathological changes improved as compared to single administration increases in one or more of the Aβ pathological change improving effects of the above-mentioned (1)-(3).

Therefore, in the medicament of the present invention, it is preferable to combine two or more compounds belonging to different clusters and described in Table 1. When compounds classified in different clusters are combined, the combination of clusters is not particularly limited as long as a superior effect compared to administration of the compound alone is achieved. For example, a combination of two or more kinds of compounds belonging to two or more clusters selected from the group consisting of clusters 1, 2, 4 and 5 is preferable. When 3 or more kinds of compounds are combined, two or more kinds of the compounds may belong to the same cluster as long as any one kind from the compounds belongs to a different cluster.

In one preferable embodiment, the medicament of the present invention may be a combination of (1) not less than two kinds of compounds belonging to two kinds of clusters (e.g., clusters 1 and 2, clusters 1 and 4, clusters 1 and 5, clusters 2 and 4, clusters 2 and 5, clusters 4 and 5), (2) not less than three kinds of compounds belonging to three kinds of clusters (e.g., clusters 1, 2 and 4, clusters 1, 2 and 5, clusters 1, 4 and 5, clusters 2, 4 and 5), or (3) not less than four kinds of compounds belonging to four kinds of clusters (clusters 1, 2, 4 and 5), each selected from the group consisting of clusters 1, 2, 4 and 5. In a more preferable embodiment, the medicament of the present invention is a combination of not less than three kinds of compounds belonging to three kinds of clusters, particularly preferably, it may be a combination of not less than three kinds of compounds belonging to clusters 1, 2 and 5 or clusters 2, 4 and 5.

In another embodiment, the medicament of the present invention may further combine, in addition to not less than two kinds of compounds belonging to two or more clusters selected from the group consisting of clusters 1, 2, 4 and 5, one or more kinds of compounds belonging to other clusters (clusters 3 and 6-10).

As compounds belonging to clusters 1, 2, 4 and 5, the following compounds can be preferably mentioned.
(a) cluster 1: Cromolyn and Niflumic acid, preferably Cromolyn
(b) cluster 2: Bromocriptine and Fluvastatin
(c) cluster 4: Probucol and Tioxolone, preferably Probucol
(d) cluster 5: Cilostazol and Topiramate Therefore, in a preferable embodiment, the medicament of the present invention is a combination of two kinds of compounds ((a) and (b), (a) and (c), (a) and (d), (b) and (c), (b) and (d), (c) and (d)), 3 kinds of compounds ((a), (b) and (c), (a), (b) and (d), (a), (c) and (d), and (b), (c) and (d)), or 4 kinds of compounds ((a), (b), (c) and (d)) selected from one or more compounds selected from the above-mentioned (a) (Cromolyn and/or Niflumic acid, preferably Cromolyn), one or more compounds selected from the above-mentioned (b) (Bromocriptine and/or Fluvastatin), one or more compounds selected from the above-mentioned (c) (Probucol and/or Tioxolone, preferably Probucol), and one or more compounds selected from the above-mentioned (d) (Cilostazol and/or Topiramate).

Further preferably, the medicament of the present invention is a combination of two or more compounds, preferably 3 or more compounds, selected from the group consisting of Bromocriptine, Cilostazol, Cromolyn, Fluvastatin, Probucol and Topiramate (provided when Bromocriptine and Fluvastatin, or Cilostazol and Topiramate are combined, one or more different compounds are desirably further combined).

Particularly preferably, the medicament of the present invention is a combination of Bromocriptine, Cromolyn and Topiramate (sometimes to be abbreviated as "BCroT"), or a combination of Bromocriptine, Cilostazol and Probucol (sometimes to be abbreviated as "BciP"), most preferably BCroT.

On the other hand, as compounds belonging to clusters 3 and 6-9, the following compounds can be preferably mentioned.
(e) cluster 3: Pinacidil and Verapamil
(f) cluster 6: Cetrimonium
(g) cluster 7: Metricrane
(h) cluster 8: Dapsone
(i) cluster 9: Chloropyramine In the medicament of the present invention, two or more compounds as active ingredients described in Table 1 may be each formulated singly or produced as a combination agent. In the former case, each preparation can be administered to the same subject simultaneously or with time lag.

The medicament of the present invention can be administered orally or parenterally in the form of the compound described in Table 1 as it is alone as the active ingredient, or as a pharmaceutical composition in an appropriate dosage form blended with a pharmaceutically acceptable carrier, excipient, diluent and the like.

As the composition for oral administration, solid or liquid dosage forms, specifically tablets (including sugar-coated tablets and film-coated tablets), pills, granules, powders, capsules (including soft capsules), syrups, emulsions, suspensions and the like can be mentioned. Meanwhile, as examples of the composition for parenteral administration, injections, suppositories and the like are used; the injections may include dosage forms such as intravenous injections, subcutaneous injections, intracutaneous injections, intramuscular injections and drip infusion injections. These preparations are produced by a well-known method using additives, including excipients (e.g., organic excipients like sugar derivatives such as lactose, sucrose, glucose, mannitol, and sorbitol; starch derivatives such as cornstarch, potato starch, a starch, and dextrin; cellulose derivatives such as crystalline cellulose; gum arabic; dextran; and pullulan; and inorganic excipients like silicate derivatives such as light anhydrous silicic acid, synthetic aluminum silicate, calcium silicate, and magnesium metasilicoaluminate; phosphates such as calcium hydrogen phosphate; carbonates such as calcium carbonate; and sulfates such as calcium sulfate), lubricants (e.g., stearic acid, metal salts of stearic acid such as calcium stearate and magnesium stearate; talc; colloidal silica; waxes such as beeswax and spermaceti; boric acid; adipic acid; sulfates such as sodium sulfate; glycol; fumaric acid; sodium benzoate; DL leucine; lauryl sulfates such as sodium lauryl sulfate and magnesium lauryl sulfate; silicates such as silicic anhydride and silicic hydrates; and the aforementioned starch derivatives), binders (e.g., hydroxypropylcellulose, hydroxypropylmethylcellulose, polyvinylpyrrolidone, macrogol, and the same compounds as the aforementioned excipients), disintegrants (e.g., cellulose derivatives such as low-substitutional hydroxypropylcellulose, carboxymethylcellulose, carboxymethylcellulose calcium, and internally crosslinked carboxymethylcellulose sodium; chemically modified starches and celluloses such as carboxymethylstarch, carboxymethylstarch sodium, and crosslinked polyvinylpyrrolidone), emulsifiers (e.g., colloidal clays such as bentonite and Veegum; metal hydroxides such as magnesium hydroxide and aluminum hydroxide; anionic surfactants such as sodium lauryl sulfate and calcium stearate; cationic surfactants such as benzalkonium chloride; and non-ionic surfactants such as polyoxyethylene alkyl ethers, polyoxyethylene sorbitan fatty acid ester, and sucrose fatty acid ester), stabilizers (para-oxybenzoic acid esters such as methyl paraben and propyl paraben; alcohols such as chlorobutanol, benzyl alcohol, and phenylethyl alcohol; benzalkonium chloride; phenols such as phenol and cresol; thimerosal; dehydroacetic acid; and sorbic acid), taste/odor correctives (e.g., sweeteners, souring agents, and flavors in common use), diluents and the like.

The administration form of the medicament of the present invention can be appropriately selected according to the dosage form thereof. For example, (1) when two or more compounds described in Table 1 are formulated as a single preparation (combination agent), the combination agent can be administered by a desired administration route. On the other hand, (2) when two or more compounds described in Table 1 are formulated separately into a concomitant drug consisting of two or more kinds of preparations, (2a) these two or more preparations may be simultaneously administered by the same administration route, (2b) these two or more preparations may be administered with time difference by the same administration route, (2c) these two or more preparations may be simultaneously administered by different administration routes, or (2d) these two or more preparations may be administered with time difference by different administration routes.

The dose of each compound described in Table 1 as the active ingredient of the medicament of the present invention may be variable according to various conditions such as the kind of compound, administration route, the symptoms, age, weight, drug receptivity of a subject and the like. For oral administration, at least 0.1 mg (suitably 0.5 mg) to at most 1000 mg (suitably 500 mg) per dose for oral administration, or at least 0.01 mg (suitably 0.05 mg) to at most 100 mg (suitably 50 mg) per dose for parenteral administration, can be administered to an adult 1 to 6 times a day. The dose may be increased or reduced according to the symptoms. Since all compounds described in Table 1 are already on the market as pharmaceutical products for diseases other than AD, an appropriate dose of each compound can be determined within the range confirmed to be safe.

For example, the information relating to the safety of the compounds described Table 1 is available from DailyMed (http://dailymed.nlm.nih.gov/dailymed/index.cfm) run by the United States National Library of Medicine.

Figure 5:
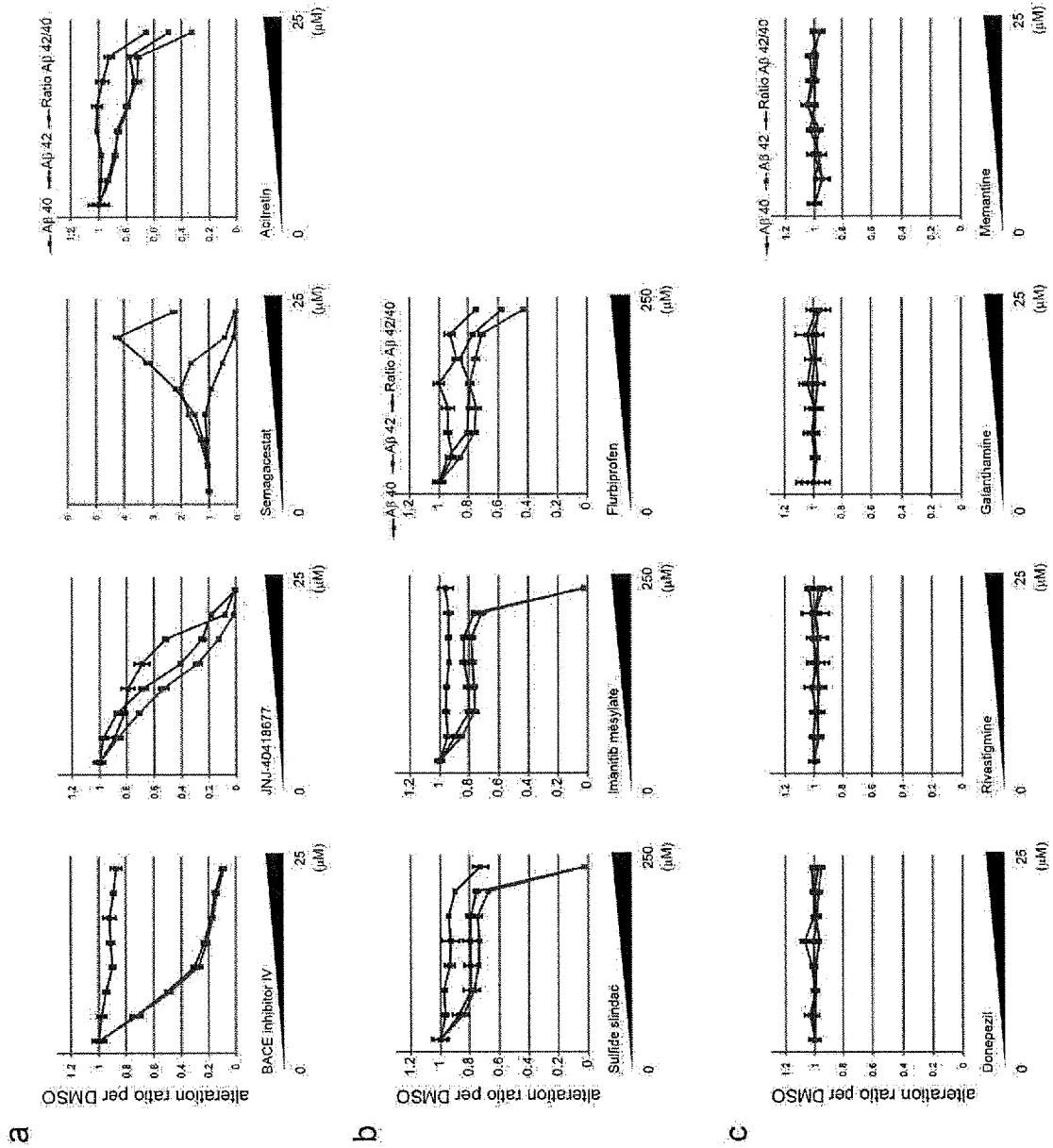

Furthermore, the medicament of the present invention may be used in combination with other drugs, for example, compounds described in FIG. 5a and known to have an Aβ pathology improving effect, existing therapeutic drugs for AD described in FIGS. 5b and 5c, preferably Donepezil and the like. The medicament of the present invention and these other drugs can be administered simultaneously, sequentially, or separately.

The present invention is explained in more detail in the following by referring to Examples, which are not to be construed as limitative.

EXAMPLES

To perform induction from iPS cells to the cerebral cortex nerve early and with high reproducibility, iPS cells introduced with human Neurogenin 2 gene (NGN2) linked to doxycycline-inducible promoter by using PiggyBac were used (FIG. 1a, FIG. 1b, FIG. 4a and FIG. 4b). IPS cells prepared from 4 patients with familial Alzheimer's disease (FAD), 2 patients with sporadic Alzheimer's disease (SAD) and 4 healthy individuals (HC) were used. The iPS cells were established by the method described in Okita K et al., Nature. 2007, vol 448, pp 313-317. It was confirmed that human iPS cells can be converted to cerebral cortical nerve by introducing NGN2 gene into these iPS cells and allowing same to transiently express for 5 days by adding doxycycline without leaving exogenous NGN2 (FIG. 1c, FIG. 4b, FIG. 4c and FIG. 4d). It was also confirmed that the converted cerebral cortical nerve induces spontaneous action potential and electric potential-dependent current (FIG. 4e). To determine the time suitable for Aβ assay, time-course changes in the amount of Aβ in the medium were analyzed, and it was confirmed that neurons on day 8 show stable Aβ secretion and sufficient maturation (FIG. 4f). Furthermore, in cerebral cortex neurons derived from patients with FAD and having mutations in PSEN1 or APP gene, it was shown that the Aβ42 amount and Aβ42/40 ratio, which are toxic Aβ, are 1.5 to 3 times higher than those of nerve cells derived from SAD patients or healthy individuals (FIG. 4f).

From the above results, as iPS cell to be used for high throughput screening (HTS), iPS cell derived from FAD patients (FAD1) having the G384A mutation of PSEN1 with the highest Aβ42/40 ratio was selected. Successively, 8 days after differentiation induction of the iPS cells into nerve cells, compounds known to lower Aβ production and Aβ42/40 ratio such as BACE inhibitor IV, JNJ-40418677, semagacestat and acitretin and the like were added and Aβ amount was confirmed two days later. As a result, it was confirmed that all the compounds improved Aβ lesion (FIG. 5a). However, Aβ42 increased with a low dose of semagacestat (FIG. 5a), and Aβ pathology was not improved with a low dose of sulindac and Flurbiprofen, which are non-steroidal antiinflammatory drugs (NSAIDs), or an anti-cancer agent imatinib having an inhibitory action on Bcr-Abl and C-kit, contrary to previous reports verifying γ-secretase regulating action by using cells overexpressing AD-related genes (FIG. 5b). Furthermore, evaluation of therapeutic drugs for AD, which have already been marketed and widely used, including cholinesterase inhibitors and NMDA blockers, showed that these symptomatic therapeutic drugs are ineffective for the improvement of Aβ pathology (FIG. 5c). From the above results, FAD1 nerve cell was confirmed to be usable for screening.

Figure 6:
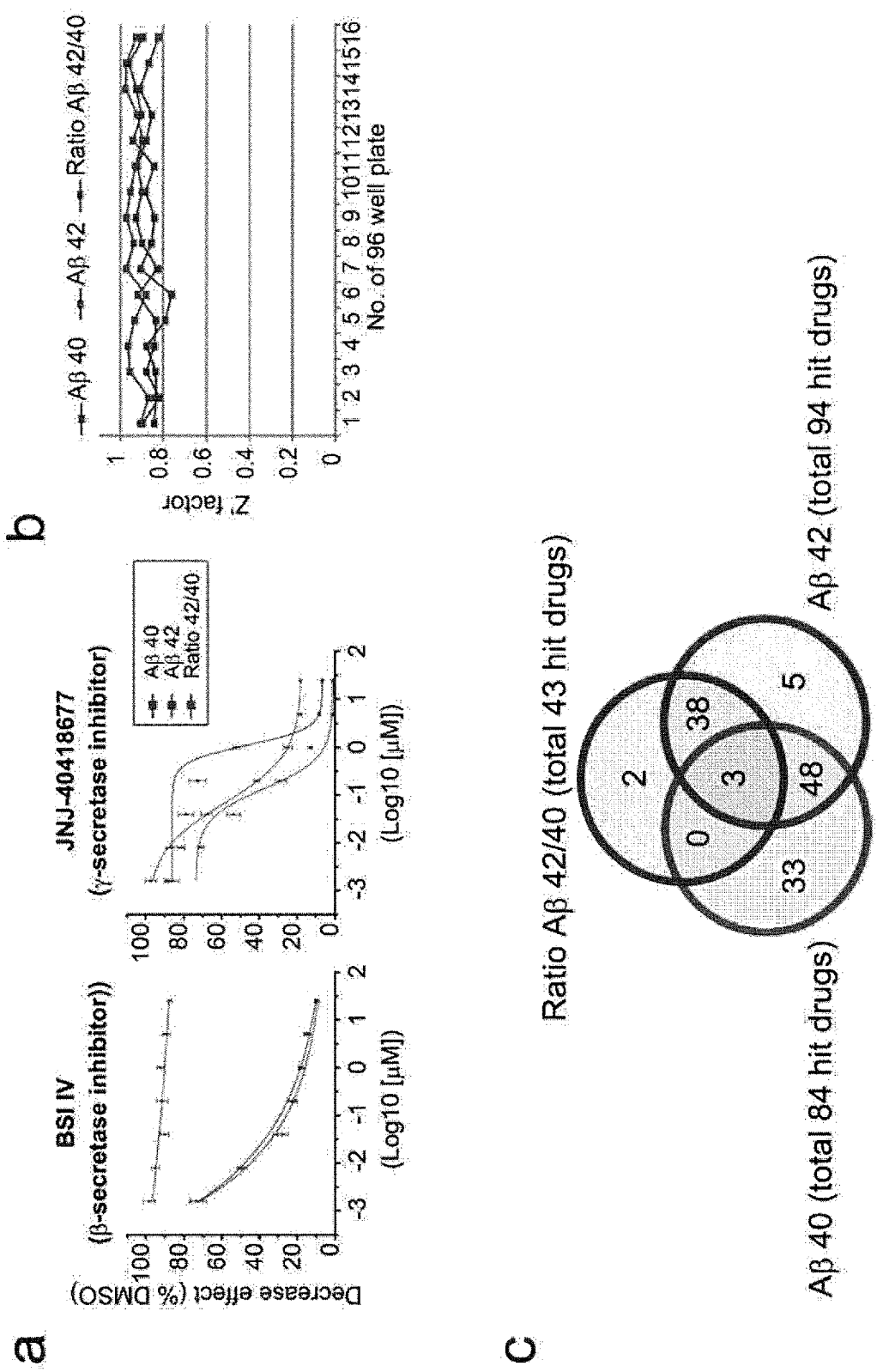

Then, existing drug library consisting of 1280 drugs approved by FDA was screened to explore drugs for improving Aβ pathology. As a negative control, 0.1% DMSO was used, as a positive control for Aβ40, 2 μM BACE inhibitor IV was used and, as a positive control for Aβ42 and Aβ42/40 ratio, 2 μM JNJ-40418677 was used. The Z' factor meaning practicability and reproducibility of HTS was not less than 0.5, thus indicating appropriate HTS (FIG. 6a and FIG. 6b). As a result of primary screening, 130 candidate compounds (since compound Nos. 14 and 124 are marketed as concomitant drugs, 129 candidate drugs) were found (FIG. 6c). Structural formulas (those in the form of salt or halide are also described as free form) and the general names of the candidate compounds are shown in Table 1.

Figure 7:
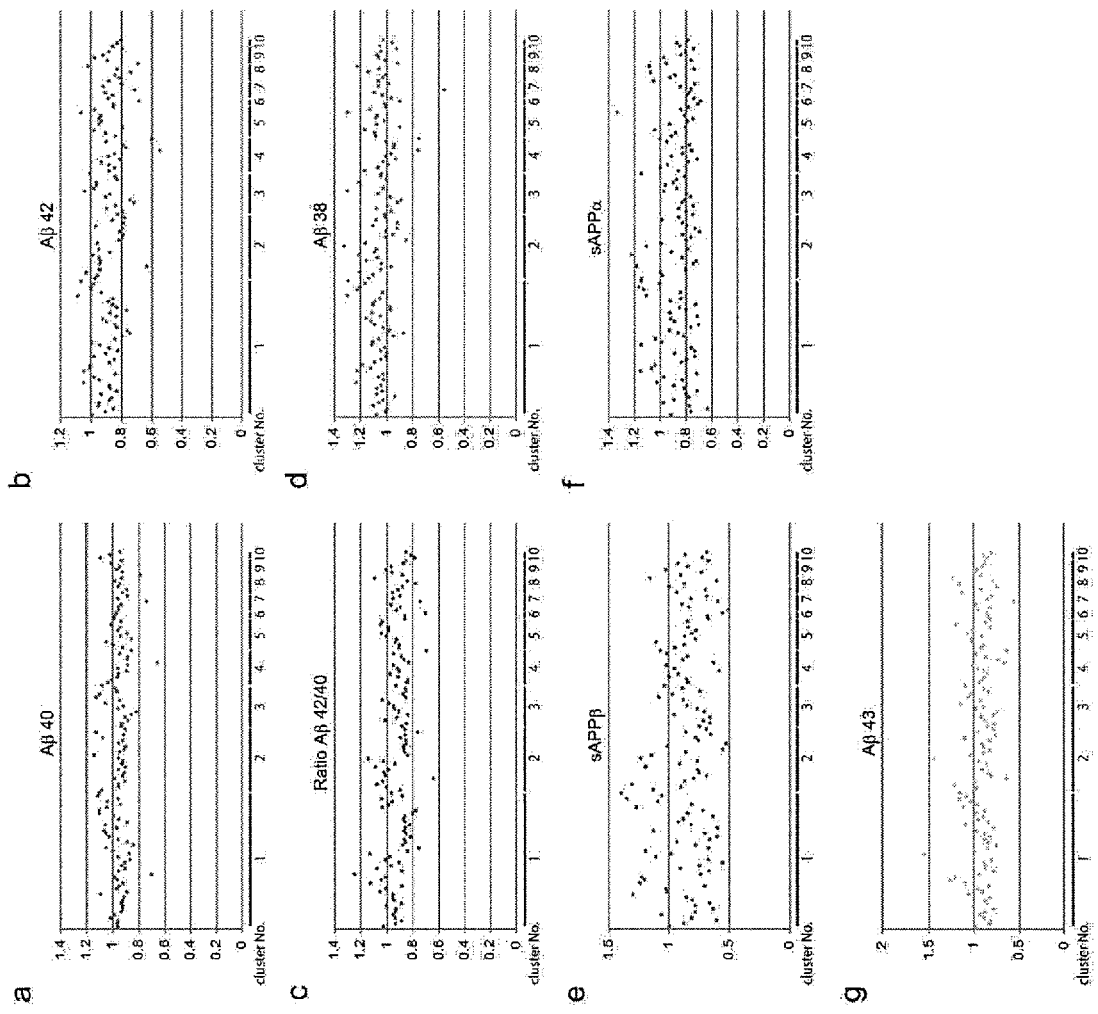
Figure 8:
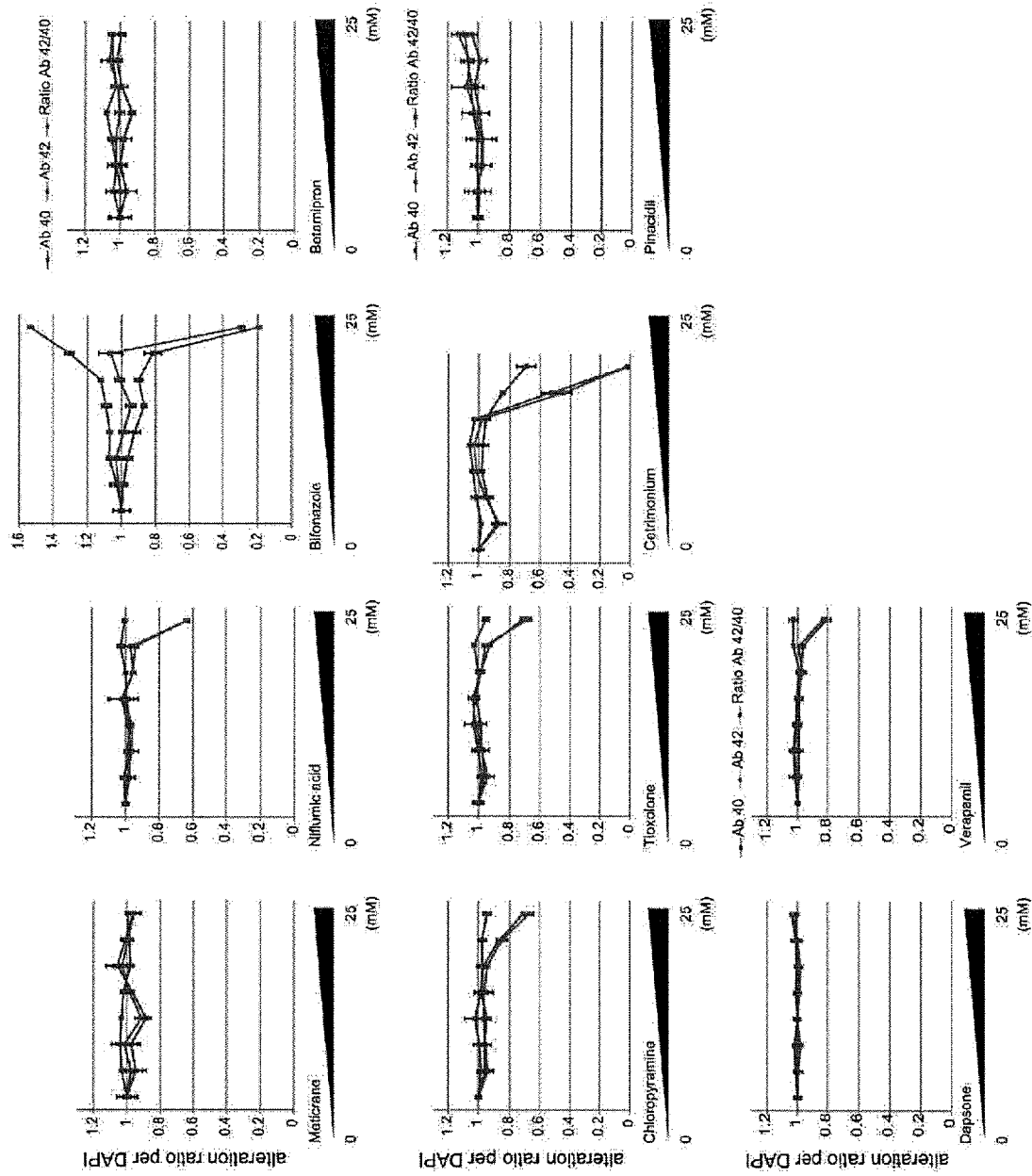
FIG. 8 FIG. 8 shows the study results of effects of Meticrane, Nifumic acid, Bifonazole, Belamipron, Chiropyramine, Tioxolone, Cetrimonum, Pinacidil, Dapsom and Verapamil on Aβ40, Aβ42 or Aβ42/Aβ40 in neuron derived from iPS cell (FAD1).

To further study reproducibility of the candidate drugs obtained by the primary screening, secondary screening was conducted. In addition to Aβ40, Aβ42, Aβ42/40 ratio, Aβ38, Aβ43, sAPPα, sAPPβ were also studied and each numerical value was obtained. The results of the above are shown in Table 2 and FIG. 7.

TABLE 2

| compound No. | cluster | compound name | Aβ40 | Aβ42 | Ratio Aβ42/40 | Aβ38 | Aβ43 | sAPPα | sAPPβ |
|---|---|---|---|---|---|---|---|---|---|
| 1 | 1 | OXYPHENCYCLIMINE HYDROCHLORIDE | 0.96 | 0.99 | 1.03 | 1.08 | 0.98 | 0.91 | 1 |

TABLE 2-continued

| compound No. | cluster | compound name | Aβ40 | Aβ42 | Ratio Aβ42/40 | Aβ38 | Aβ43 | sAPPα | sAPPβ |
|---|---|---|---|---|---|---|---|---|---|
| 2 | 1 | MEPIVACAINE HYDROCHLORIDE | 0.97 | 0.9 | 0.93 | 1.01 | 0.83 | 0.77 | 0.88 |
| 3 | 1 | RANOLAZINE | 0.96 | 0.85 | 0.89 | 1 | 0.82 | 0.64 | 0.61 |
| 4 | 1 | ATOMOXETINE HYDROCHLORIDE | 1.02 | 0.95 | 0.94 | 1.1 | 0.89 | 0.78 | 0.81 |
| 5 | 1 | TERBINAFINE HYDROCHLORIDE | 0.99 | 0.94 | 0.96 | 1.06 | 0.94 | 0.98 | 1.06 |
| 6 | 1 | LOPERAMIDE HYDROCHLORIDE | 0.94 | 0.88 | 0.93 | 1.03 | 0.88 | 0.89 | 0.78 |
| 7 | 1 | ALVERINE CITRATE | 0.93 | 0.86 | 0.93 | 0.94 | 0.79 | 0.78 | 0.63 |
| 8 | 1 | APOMORPHINE HYDROCHLORIDE | 0.93 | 0.93 | 1.01 | 1.08 | 1.01 | 0.8 | 0.78 |
| 9 | 1 | CLOMIPHENE CITRATE | 0.93 | 0.83 | 0.89 | 1.04 | 0.86 | 0.71 | 0.66 |
| 10 | 1 | COTININE | 0.92 | 0.87 | 0.94 | 1.08 | 0.87 | 0.81 | 0.81 |
| 11 | 1 | CROMOLYN SODIUM | 0.92 | 0.88 | 0.96 | 1.04 | 0.82 | 0.89 | 0.86 |
| 12 | 1 | CYCLIZINE | 1.09 | 1.04 | 0.95 | 1.23 | 1.06 | 1.03 | 1.3 |
| 13 | 1 | DESIPRAMINE HYDROCHLORIDE | 0.89 | 0.94 | 1.06 | 1.02 | 0.9 | 0.83 | 1.01 |
| 14 | 1 | diphenhydramine (combinated compounds of "DIMENHYDRINATE") | 0.97 | 0.98 | 1.01 | 1.06 | 0.97 | 0.97 | 1.02 |
| 15 | 1 | ETHOPROPAZINE HYDROCHLORIDE | 0.95 | 0.84 | 0.88 | 1.03 | 0.84 | 0.72 | 0.71 |
| 16 | 1 | HOMATROPINE BROMIDE | 0.92 | 1.04 | 1.13 | 1.22 | 1.09 | 1.15 | 1.24 |
| 17 | 1 | IMIPRAMINE HYDROCHLORIDE | 0.97 | 1.01 | 1.05 | 1.12 | 1.27 | 1.07 | 1.2 |
| 18 | 1 | TACRINE HYDROCHLORIDE | 0.99 | 1 | 1.02 | 1.18 | 1.21 | 1.04 | 1.23 |
| 19 | 1 | ISOPROPAMIDE IODIDE | 0.71 | 0.88 | 1.24 | 1.09 | 0.95 | 0.84 | 0.74 |
| 20 | 1 | THIABENDAZOLE | 0.96 | 0.84 | 0.88 | 1.05 | 0.79 | 0.79 | 0.67 |
| 21 | 1 | BETAHISTINE HYDROCHLORIDE | 0.91 | 0.98 | 1.08 | 1.01 | 0.87 | 0.73 | 0.91 |
| 22 | 1 | VESAMICOL HYDROCHLORIDE | 0.93 | 0.9 | 0.97 | 1 | 0.87 | 0.89 | 0.74 |
| 23 | 1 | MONOBENZONE | 0.91 | 0.82 | 0.91 | 1.05 | 0.89 | 0.74 | 0.56 |
| 24 | 1 | CINCHONINE | 0.87 | 0.88 | 1.01 | 1.02 | 0.81 | 0.76 | 0.68 |
| 25 | 1 | LOXAPINE SUCCINATE | 0.96 | 0.94 | 0.98 | 1.11 | 1.14 | 1.15 | 1.11 |
| 26 | 1 | ETODOLAC | 0.88 | 0.99 | 1.13 | 1.11 | 1.55 | 0.99 | 0.98 |
| 27 | 1 | BIFONAZOLE | 1 | 0.84 | 0.84 | 1.06 | 0.99 | 1.04 | 1.19 |
| 28 | 1 | NOMIFENSINE MALEATE | 1.05 | 0.8 | 0.75 | 0.95 | 0.85 | 0.82 | 0.67 |
| 29 | 1 | CARBADOX | 0.84 | 0.74 | 0.88 | 0.87 | 0.76 | 0.86 | 0.78 |
| 30 | 1 | LEVOCETIRIZINE DIHYDROCHLORIDE | 0.89 | 0.76 | 0.85 | 0.98 | 0.85 | 0.93 | 0.93 |
| 31 | 1 | METITEPINE MALEATE | 0.96 | 0.83 | 0.86 | 1.03 | 0.88 | 0.76 | 0.66 |
| 32 | 1 | BETAMIPRON | 1.03 | 0.84 | 0.82 | 1.1 | 0.82 | 0.7 | 0.6 |
| 33 | 1 | CAMYLOFINE DIHYDROCHLORIDE | 1.05 | 0.9 | 0.85 | 1.12 | 0.88 | 0.89 | 0.71 |
| 34 | 1 | NIALAMIDE | 1.06 | 0.92 | 0.87 | 1.16 | 0.97 | 0.92 | 1.13 |
| 35 | 1 | CHINIOFON | 0.97 | 0.83 | 0.86 | 1.05 | 0.79 | 0.71 | 0.6 |
| 36 | 1 | PIRIBEDIL HYDROCHLORIDE | 1.06 | 0.87 | 0.83 | 1.11 | 1.09 | 0.92 | 0.82 |
| 37 | 1 | NIFLUMIC ACID | 0.89 | 0.77 | 0.86 | 0.97 | 0.85 | 0.8 | 0.92 |
| 38 | 1 | CYPERMETHRIN | 0.95 | 0.83 | 0.87 | 0.97 | 0.95 | 0.85 | 0.88 |
| 39 | 1 | NAFTOPIDIL | 1 | 0.86 | 0.86 | 1.1 | 0.9 | 0.73 | 0.64 |
| 40 | 1 | CYCLANDELATE | 1.1 | 0.88 | 0.8 | 1.09 | 0.98 | 0.92 | 0.84 |
| 41 | 1 | QUININE ETHYL CARBONATE | 1.1 | 0.85 | 0.77 | 1.05 | 0.88 | 0.84 | 0.72 |
| 42 | 1 | PIPENZOLATE BROMIDE | 1.05 | 1 | 1.04 | 1.3 | 1.12 | 1.11 | 1.27 |
| 43 | 1 | IDAZOXAN HYDROCHLORIDE | 0.94 | 0.93 | 0.99 | 1.03 | 0.97 | 0.84 | 0.81 |
| 44 | 1 | IFENPRODIL TARTRATE | 1.04 | 1 | 0.96 | 1.23 | 1.03 | 1.13 | 1.09 |
| 45 | 1 | EBSELEN | 0.96 | 1 | 1.04 | 1.2 | 1.16 | 1.17 | 1.35 |
| 46 | 2 | LOVASTATIN | 1.11 | 0.98 | 0.88 | 1.17 | 1.09 | 1.01 | 1.06 |
| 47 | 2 | AMINOLEVULINIC ACID HYDROCHLORIDE | 1.1 | 1.06 | 0.97 | 1.29 | 1.16 | 1.15 | 1.4 |
| 48 | 2 | VALSARTAN | 1.08 | 0.97 | 0.9 | 1.14 | 1 | 1.14 | 1.13 |
| 49 | 2 | AMINOCAPROIC ACID | 0.95 | 0.96 | 1 | 1.1 | 0.97 | 0.99 | 0.9 |
| 50 | 2 | AMINOSALICYLATE SODIUM | 0.96 | 1.03 | 1.08 | 1.2 | 1.22 | 1 | 1.31 |
| 51 | 2 | BENZOCAINE | 0.91 | 0.94 | 1.03 | 1.05 | 0.99 | 0.8 | 0.87 |
| 52 | 2 | BROMOCRIPTINE MESYLATE | 0.99 | 0.63 | 0.64 | 0.97 | 0.65 | 1.18 | 0.79 |
| 53 | 2 | BUTYL PARABEN | 0.92 | 0.94 | 1.02 | 1.04 | 0.81 | 0.74 | 0.69 |
| 54 | 2 | DIOXYBENZONE | 0.91 | 0.93 | 1.02 | 1.16 | 0.83 | 0.72 | 0.75 |
| 55 | 2 | DYCLONINE HYDROCHLORIDE | 0.96 | 0.94 | 0.99 | 1.07 | 0.9 | 0.83 | 0.76 |
| 56 | 2 | CALCIUM GLUCEPTATE | 0.9 | 0.98 | 1.09 | 1.21 | 1.32 | 1.22 | 1.19 |
| 57 | 2 | CAPTOPRIL | 0.93 | 0.87 | 0.94 | 1.09 | 0.86 | 0.91 | 0.91 |
| 58 | 2 | BUTAMBEN | 0.92 | 0.95 | 1.03 | 1.08 | 0.95 | 0.79 | 0.76 |
| 59 | 2 | BACAMPICILLIN HYDROCHLORIDE | 0.95 | 1.09 | 1.15 | 1.32 | 1.44 | 1.11 | 1.23 |
| 60 | 2 | FLUVASTATIN | 1.14 | 0.96 | 0.84 | 1.16 | 1.04 | 0.99 | 1.14 |
| 61 | 2 | OLMESARTAN MEDOXOMIL | 0.95 | 0.82 | 0.86 | 0.85 | 0.9 | 0.8 | 0.86 |
| 62 | 2 | CEFTIBUTEN | 0.91 | 0.79 | 0.87 | 1.01 | 0.83 | 0.76 | 0.55 |
| 63 | 2 | CEFDINIR | 0.9 | 0.79 | 0.87 | 0.95 | 0.9 | 0.82 | 1.01 |
| 64 | 2 | PERINDOPRIL ERBUMINE | 0.95 | 0.81 | 0.85 | 1.01 | 0.91 | 0.7 | 0.53 |
| 65 | 2 | ZOMEPIRAC SODIUM | 0.93 | 0.79 | 0.85 | 0.92 | 0.83 | 0.73 | 0.76 |
| 66 | 2 | CEFAMANDOLE NAFATE | 1.08 | 0.97 | 0.9 | 1.11 | 1.11 | 0.79 | 0.78 |
| 67 | 2 | HYDROXYTOLUIC ACID | 0.92 | 0.79 | 0.86 | 0.92 | 0.77 | 0.83 | 0.66 |
| 68 | 2 | DIACETAMATE | 1.13 | 0.86 | 0.76 | 1.08 | 0.97 | 0.98 | 0.86 |
| 69 | 2 | PIROMIDIC ACID | 0.91 | 0.78 | 0.86 | 1.01 | 0.79 | 0.86 | 0.69 |
| 70 | 2 | BUCETIN | 0.93 | 0.82 | 0.88 | 1.02 | 0.85 | 0.75 | 0.75 |
| 71 | 2 | REBAMIPIDE | 0.93 | 0.79 | 0.85 | 0.97 | 0.78 | 0.8 | 0.66 |
| 72 | 3 | HYDROXYCHLOROQUINE SULFATE | 0.88 | 0.9 | 1.01 | 1.08 | 0.87 | 0.85 | 0.72 |
| 73 | 3 | LEVALBUTEROL HYDROCHLORIDE | 0.91 | 0.84 | 0.92 | 0.99 | 0.91 | 0.74 | 0.66 |
| 74 | 3 | PINACIDIL | 0.86 | 0.72 | 0.84 | 0.92 | 0.79 | 0.83 | 0.96 |
| 75 | 3 | VERAPAMIL HYDROCHLORIDE | 0.82 | 0.74 | 0.91 | 0.89 | 0.75 | 0.81 | 0.71 |

TABLE 2-continued

| compound No. | cluster | compound name | Aβ40 | Aβ42 | Ratio Aβ42/40 | Aβ38 | Aβ43 | sAPPα | sAPPβ |
|---|---|---|---|---|---|---|---|---|---|
| 76 | 3 | DIBUCAINE HYDROCHLORIDE | 0.96 | 0.9 | 0.94 | 0.97 | 0.98 | 0.77 | 0.77 |
| 77 | 3 | PRIMAQUINE DIPHOSPHATE | 0.92 | 0.87 | 0.95 | 1.07 | 0.89 | 0.79 | 0.85 |
| 78 | 3 | NIZATIDINE | 1.06 | 1.04 | 0.98 | 1.3 | 1.15 | 0.97 | 1.29 |
| 79 | 3 | CIMETIDINE | 0.95 | 0.98 | 1.04 | 1.03 | 0.92 | 0.87 | 0.88 |
| 80 | 3 | RIZATRIPTAN BENZOATE | 1.13 | 0.96 | 0.85 | 1.2 | 1.07 | 0.96 | 1.08 |
| 81 | 3 | ALFLUZOSIN | 1.1 | 0.96 | 0.87 | 1.22 | 1.03 | 0.9 | 0.97 |
| 82 | 3 | TULOBUTEROL | 0.97 | 0.83 | 0.85 | 1 | 0.84 | 0.87 | 0.74 |
| 83 | 3 | NIMUSTINE | 0.98 | 0.84 | 0.86 | 1.04 | 0.89 | 0.81 | 0.89 |
| 84 | 3 | TRIMETAZIDINE DIHYDROCHLORIDE | 1.08 | 1.01 | 0.93 | 1.04 | 1.09 | 1.15 | 1.04 |
| 85 | 3 | CLENBUTEROL HYDROCHLORIDE | 1.04 | 0.88 | 0.85 | 1.17 | 0.94 | 0.86 | 0.84 |
| 86 | 3 | BROMOPRIDE | 1.01 | 0.84 | 0.84 | 1.07 | 0.9 | 1 | 0.85 |
| 87 | 4 | PROPOFOL | 0.96 | 0.88 | 0.91 | 0.99 | 0.88 | 0.94 | 1 |
| 88 | 4 | BITHIONATE SODIUM | 0.96 | 0.93 | 0.97 | 1.03 | 0.85 | 0.78 | 0.92 |
| 89 | 4 | CRESOL | 0.89 | 0.81 | 0.91 | 0.93 | 0.89 | 0.71 | 0.58 |
| 90 | 4 | DOPAMINE HYDROCHLORIDE | 0.96 | 0.88 | 0.92 | 1.01 | 0.96 | 0.91 | 0.95 |
| 91 | 4 | TRIOXSALEN | 0.89 | 0.84 | 0.95 | 0.97 | 1.01 | 0.82 | 1.02 |
| 92 | 4 | TIOXOLONE | 0.66 | 0.55 | 0.83 | 0.76 | 0.67 | 0.76 | 0.63 |
| 93 | 4 | METACETAMOL | 0.89 | 0.77 | 0.86 | 0.95 | 0.74 | 0.83 | 0.89 |
| 94 | 4 | DICHLOROPHENE | 0.89 | 0.79 | 0.89 | 0.94 | 0.87 | 0.78 | 0.85 |
| 95 | 4 | DINITOLMIDE | 0.95 | 0.9 | 0.95 | 1 | 0.98 | 0.95 | 1.02 |
| 96 | 4 | PROBUCOL | 0.86 | 0.6 | 0.7 | 0.75 | 0.65 | 1 | 1.07 |
| 97 | 5 | RIFAXIMIN | 0.92 | 0.84 | 0.91 | 1.09 | 0.92 | 0.91 | 0.95 |
| 98 | 5 | DESOXYCORTICOSTERONE ACETATE | 1 | 0.9 | 0.9 | 1.09 | 0.89 | 0.88 | 0.87 |
| 99 | 5 | TRAMADOL HYDROCHLORIDE | 1.05 | 0.98 | 0.93 | 1.17 | 1.02 | 1.04 | 1.11 |
| 100 | 5 | TOPIRAMATE | 0.86 | 0.79 | 0.92 | 0.9 | 1.02 | 0.81 | 0.78 |
| 101 | 5 | CAMPHOR (1R) | 0.94 | 0.95 | 1.01 | 1.08 | 0.91 | 0.92 | 0.87 |
| 102 | 5 | DANAZOL | 0.89 | 0.93 | 1.04 | 1.02 | 1.07 | 0.79 | 0.81 |
| 103 | 5 | SODIUM DEHYDROCHOLATE | 0.96 | 0.95 | 0.99 | 1.09 | 1.01 | 0.75 | 0.78 |
| 104 | 5 | DICYCLOMINE HYDROCHLORIDE | 0.94 | 0.93 | 0.99 | 1.08 | 0.82 | 0.81 | 0.84 |
| 105 | 5 | VANCOMYCIN HYDROCHLORIDE | 1.01 | 1.06 | 1.05 | 1.29 | 1.2 | 1.33 | 1.36 |
| 106 | 5 | BRUCINE | 0.94 | 0.98 | 1.04 | 1.13 | 0.87 | 0.84 | 0.85 |
| 107 | 5 | CILOSTAZOL | 0.99 | 0.85 | 0.86 | 1.01 | 0.82 | 0.78 | 0.68 |
| 108 | 5 | TELITHROMYCIN | 0.99 | 0.85 | 0.86 | 1.02 | 0.84 | 0.71 | 0.68 |
| 109 | 5 | PRASTERONE ACETATE | 0.97 | 0.68 | 0.7 | 0.9 | 0.85 | 0.69 | 0.55 |
| 110 | 5 | TROXERUTIN | 0.96 | 0.88 | 0.93 | 0.97 | 0.95 | 0.74 | 0.51 |
| 111 | 6 | DOCOSANOL | 0.96 | 0.86 | 0.9 | 1.03 | 0.83 | 0.79 | 0.83 |
| 112 | 6 | DISULFIRAM | 0.94 | 0.91 | 0.97 | 1.1 | 0.98 | 0.78 | 0.89 |
| 113 | 6 | CETRIMONIUM BROMIDE | 0.74 | 0.71 | 0.74 | 0.56 | 0.56 | 0.76 | 0.59 |
| 114 | 7 | CYCLOSERINE | 0.96 | 0.92 | 0.95 | 1.06 | 0.85 | 0.84 | 0.82 |
| 115 | 7 | CYTARABINE | 0.89 | 0.8 | 0.9 | 0.99 | 0.81 | 0.74 | 0.69 |
| 116 | 7 | ALLANTOIN | 0.92 | 0.88 | 0.96 | 1.07 | 1.13 | 1.05 | 0.93 |
| 117 | 7 | ALTHIAZIDE | 0.89 | 0.81 | 0.91 | 1.03 | 0.91 | 0.92 | 0.7 |
| 118 | 7 | CLAVULANATE LITHIUM | 0.96 | 0.84 | 0.88 | 1.01 | 0.75 | 0.88 | 1 |
| 119 | 7 | METICRANE | 0.95 | 0.74 | 0.78 | 1.14 | 1.16 | 1.07 | 0.87 |
| 120 | 8 | DAPSONE | 0.98 | 0.83 | 0.84 | 1.06 | 0.8 | 0.74 | 0.6 |
| 121 | 8 | HISTAMINE DIHYDROCHLORIDE | 0.93 | 1.02 | 1.09 | 1.22 | 1.23 | 1.08 | 1.15 |
| 122 | 8 | THIOGUANINE | 0.79 | 0.69 | 0.88 | 0.91 | 0.92 | 0.95 | 0.9 |
| 123 | 8 | BITOSCANATE | 0.93 | 0.89 | 0.96 | 1.01 | 1 | 0.76 | 0.73 |
| 124 | 9 | 8-chlorotheophylline (combinated compounds of "DIMENHYDRINATE") | 0.97 | 0.98 | 1.01 | 1.06 | 0.97 | 0.97 | 1.02 |
| 125 | 9 | DIAZOXIDE | 0.95 | 0.92 | 0.97 | 1.08 | 0.9 | 0.84 | 0.84 |
| 126 | 9 | SIBUTRAMINE HYDROCHLORIDE | 1.01 | 0.88 | 0.87 | 1.05 | 0.87 | 0.8 | 0.92 |
| 127 | 9 | CHLORINDIONE | 0.93 | 0.79 | 0.85 | 0.92 | 0.87 | 0.74 | 0.67 |
| 128 | 9 | CHLORMEZANONE | 1.09 | 0.86 | 0.78 | 1.05 | 0.85 | 0.85 | 0.72 |
| 129 | 9 | CHLOROPYRAMINE HYDROCHLORIDE | 1.02 | 0.83 | 0.81 | 0.96 | 0.89 | 0.87 | 0.86 |
| 130 | 10 | FLUROTHYL | 0.94 | 0.8 | 0.85 | 1.03 | 0.81 | 0.79 | 0.69 |

The importance of combination therapy has been studied in various fields in recent years. To achieve a synergistic effect, combinations of drugs with higher differences rather than combination of similar compounds were examined. The drug structures were converted to "Finger printing" information using ECFP4 method (Rogers D et al. J Chem Inf Model. 2010 24; 50(5):742-54.) suitable for computer processing, and similarity depending on the structural formulas was studied through clustering analysis based on distance matrix, and Non bias classification not relying on known efficacy was tried. As a result, 129 candidate drugs were classified into 10 Clusters. The results are shown in Table 2 and FIG. 2b.

Figures 1, 3:
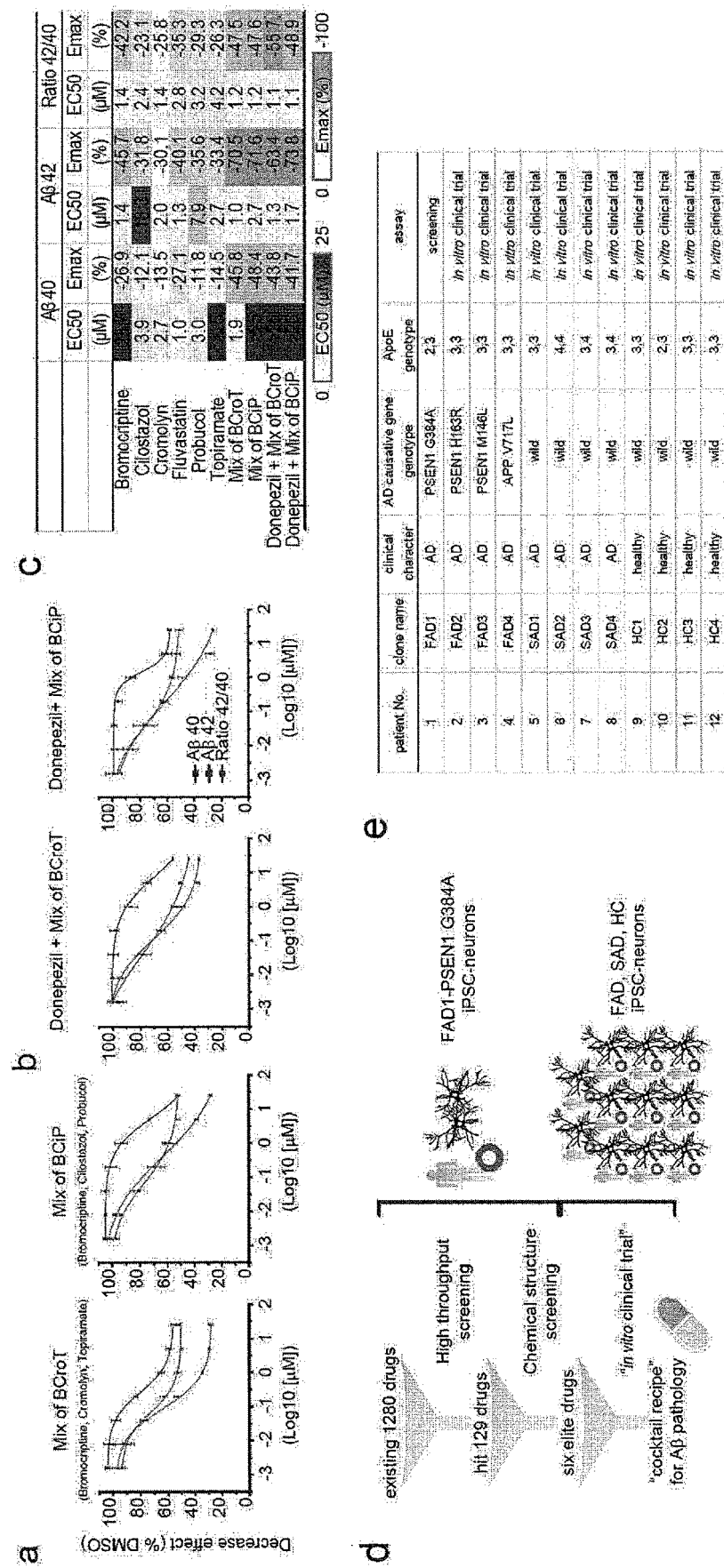
Figures 2, 3:
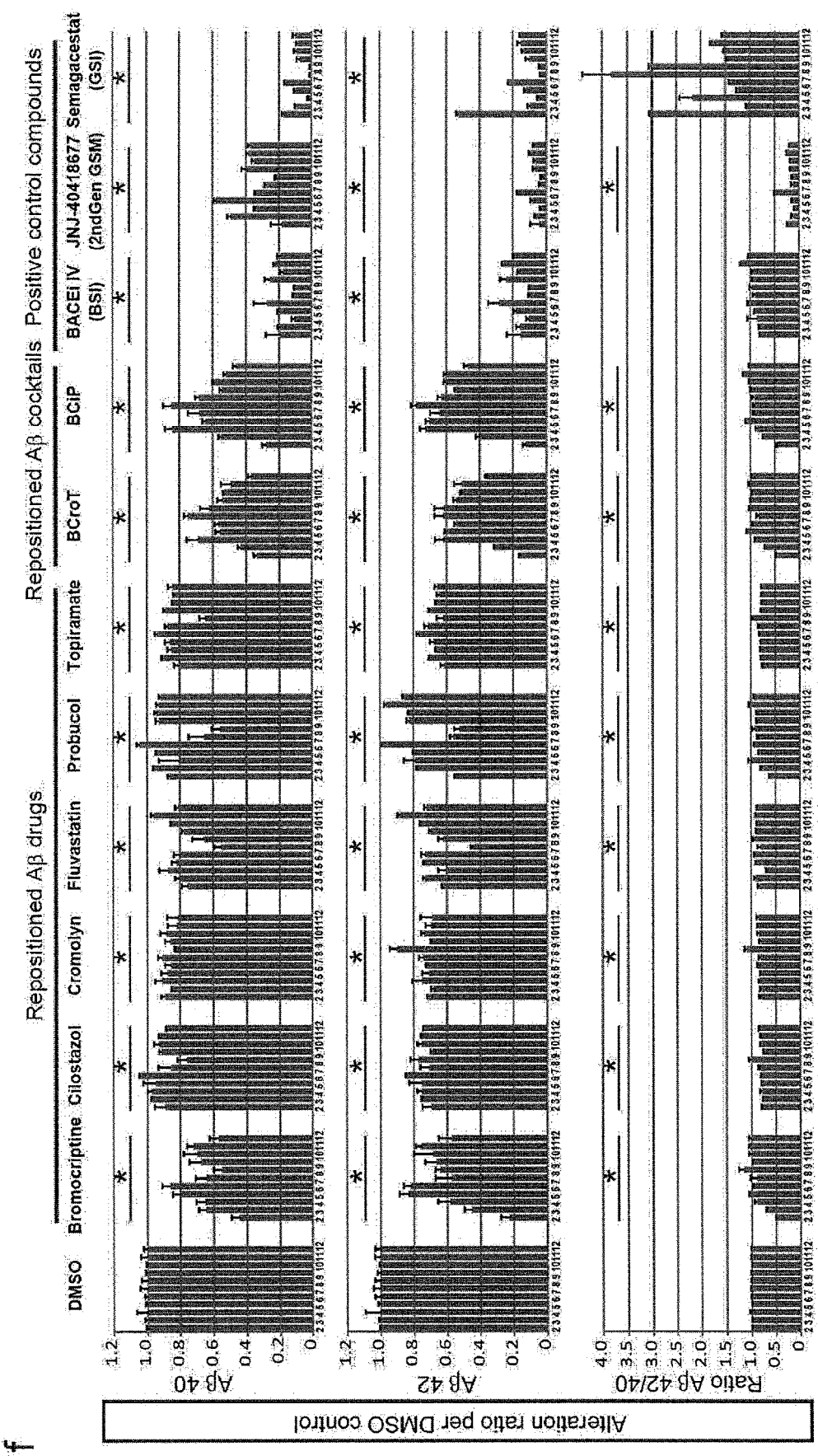
Figure 3:
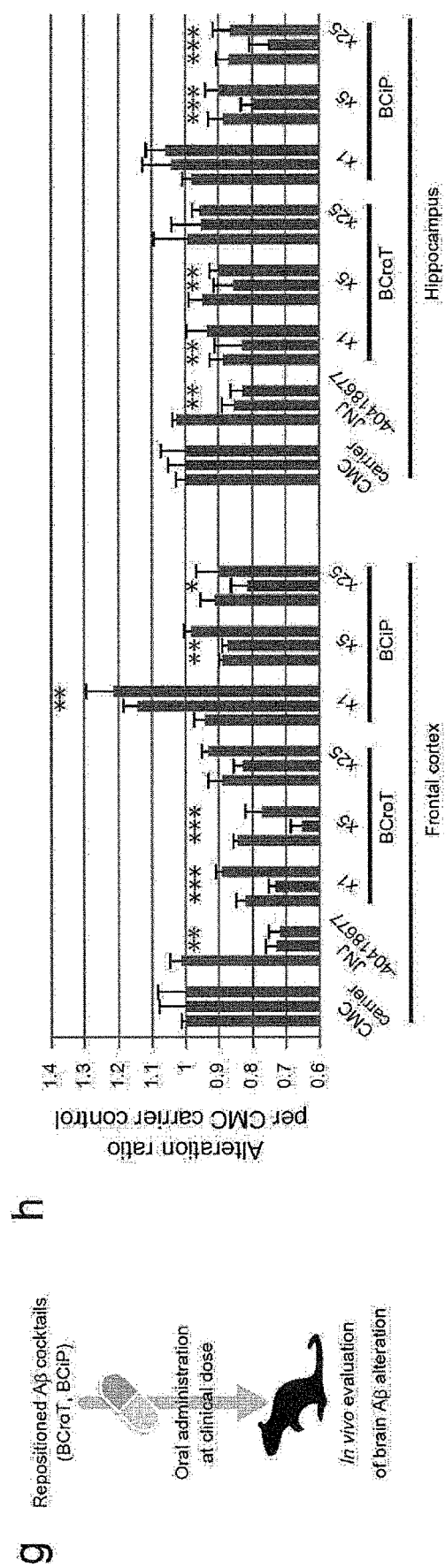
Figure 4:
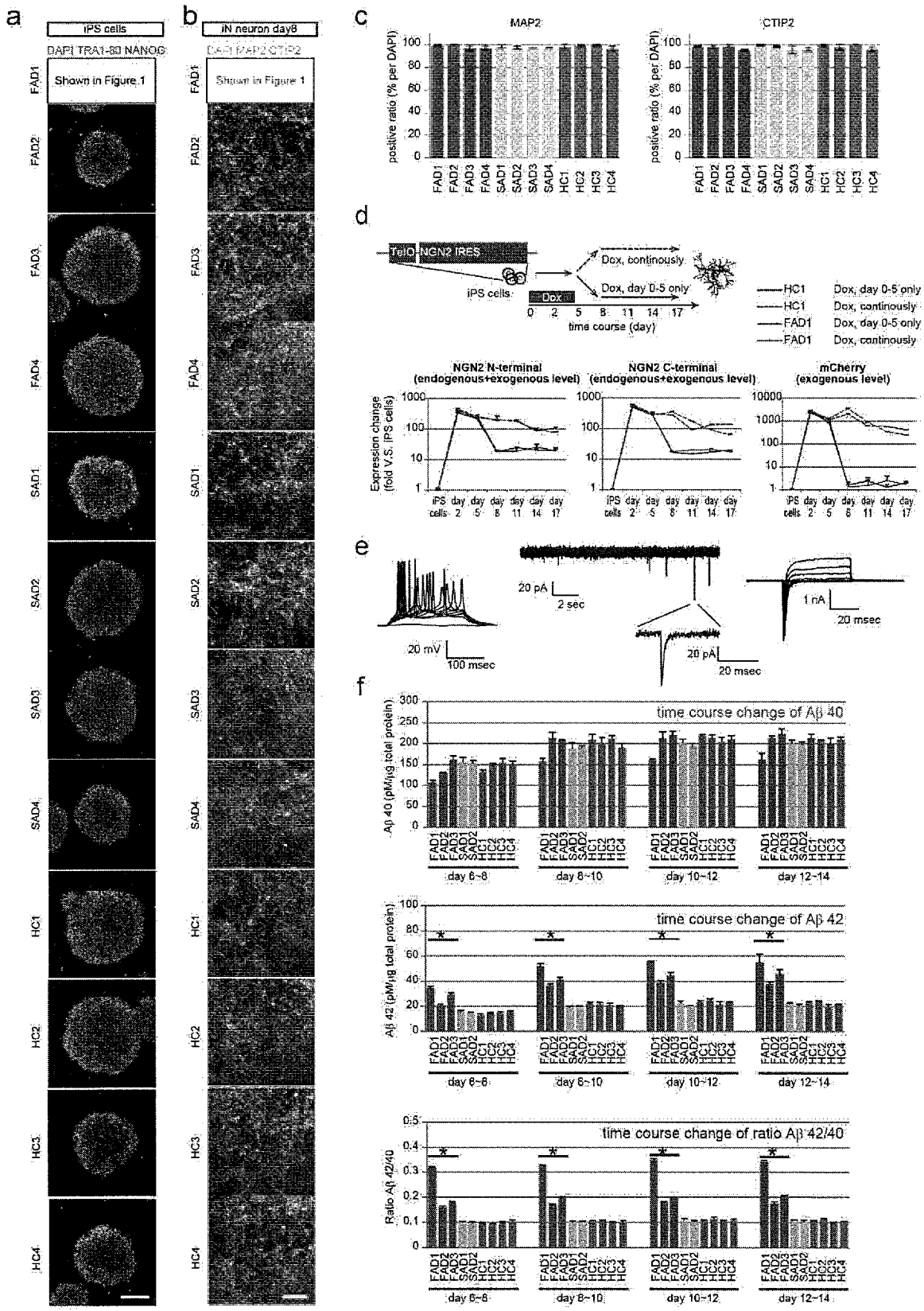
Figure 9:
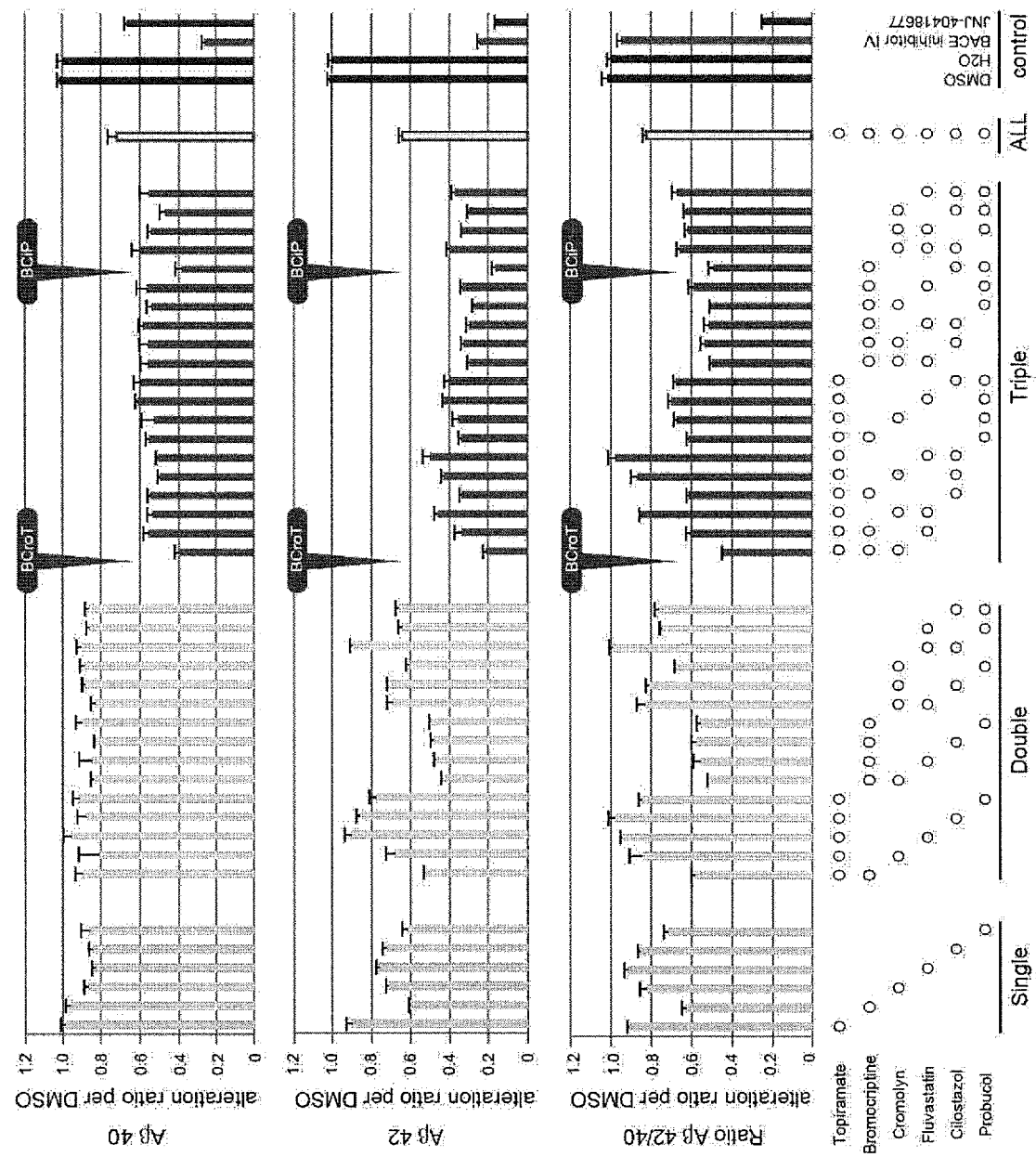
FIG. 9 FIG. 9 shows effects of Topiramate, Bromocriptine, Cromolyn, Fluvastatin, Cilostazol and Probucol as single agents and combinations of 2 agents, 3 agents or all agents on Aβ40, Aβ42 or Aβ42/Aβ40 ratio.
Figure 10:
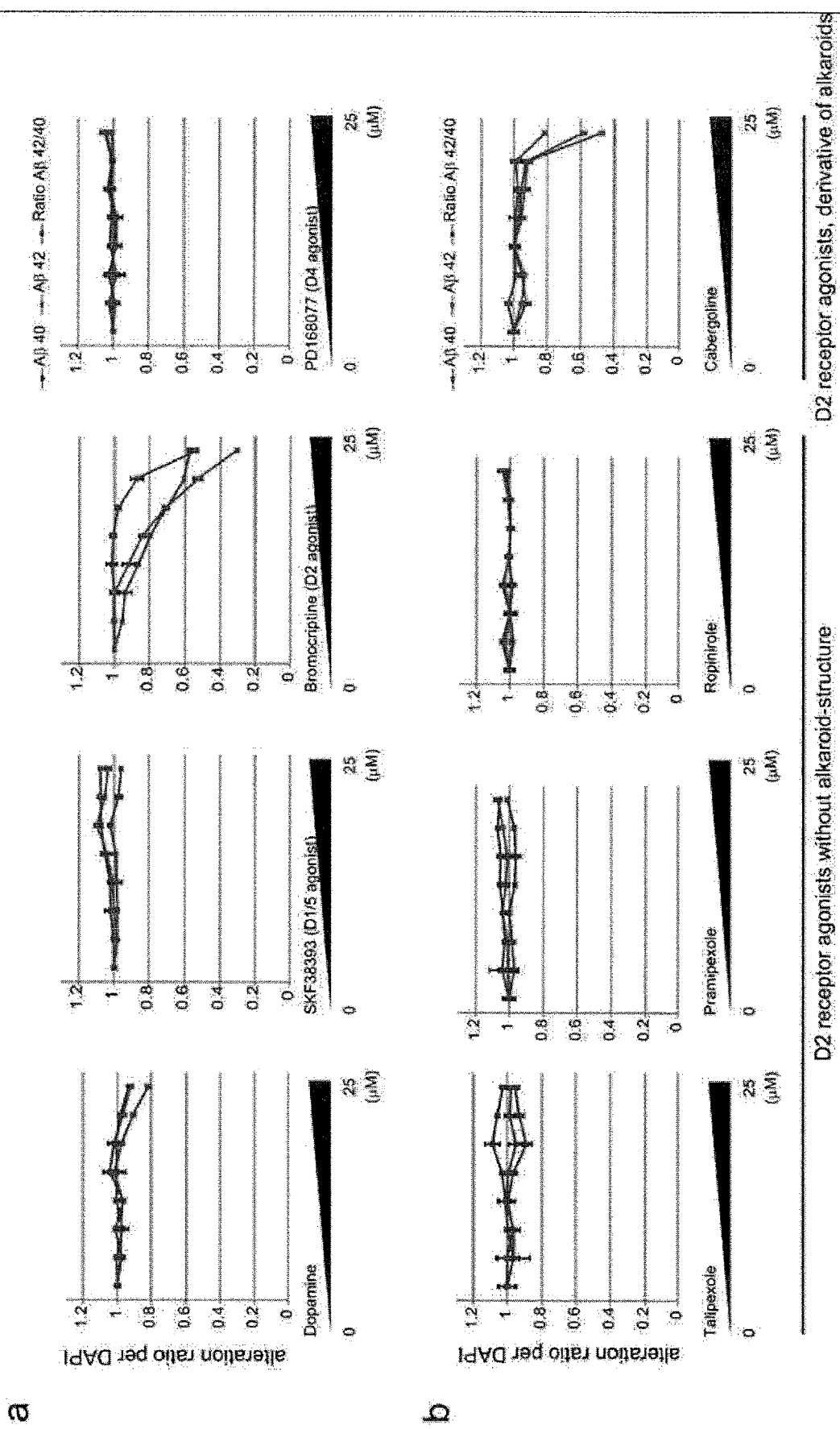

Drugs with large Aβ change rate based on the numerical values obtained by the secondary screening and drugs classified in different clusters were selected, and dose-dependent reactivity was also found using a compound having the same structure and obtained from a different supplyer (FIG. 2c). Six kinds of existing drugs with particularly low $EC_{50}$ and high $E_{max}$ were selected as the best. Furthermore, in view of central nervous system permeability and suitability for the age receiving administration as a pre-emptive medicine, two kinds of existing drug cocktails, Bromocriptine, Cromolyn and Topiramate (BCroT) and Bromocriptine, Cilostazol and Probucol (BCiP) were found (FIG. 3a, FIG. 9). As a result of use of different clusters in chemical clustering (FIG. 2b), they were found to act additively compared to single agents (FIG. 3a, FIG. 9). Furthermore, they were found to increase $EC_{50}$ of Aβ40 recognized as wild-type or Protective Aβ in combination with Donepezil, which is the most widely used therapeutic drug for AD (FIG. 3b, c).

Moreover, cerebral cortex nerve cells were produced from iPS cells (FIG. 4a) established from a total of 11 different individuals including FAD.SAD patients and healthy individuals at the time of somatic cell biopsy (FIG. 3d, e, Table 3) similarly by forced NGN2 expression (FIGS. 4b, c), and 6 kinds of selected best existing drugs and cocktail of BCroT, BCiP were administered. As a result, Aβ treatment effects thereof were found (FIG. 3f).

TABLE 3

| clone name | gender | onset (age) | biopsy (age) | genotype APP | PSENI | APOE | clone name at establishment | origin cell | reprogramming method | karyotype | in vitro differentiation |
|---|---|---|---|---|---|---|---|---|---|---|---|
| FAD1 | female | 38 | 41 | wild | G384A | 2, 3 | AD2P212 | fibroblast | epi, OSKMLshp53 | 46 XX | yes |
| FAD2 | male | 47 | 47 | wild | H163R | 3, 3 | AD15E11 | fibroblast | epi, OSKMLshp53 | 46 XY | yes |
| FAD3 | male | N.A | 53 | wild | M146L | 3, 3 | AG07872E1 | fibroblast | epi, OSKMLshp53 | 46 XY | yes |
| FAD4 | female | 45 | 57 | V717L | wild | 3, 3 | APP2E22 | fibroblast | epi, OSKMLshp53 | 46 XX | yes |
| SAD1 | male | 60 | 55 | wild | wild | 3, 3 | AD3E211 | fibroblast | epi, OSKMLshp53 | 46 XY | yes |
| SAD2 | male | 56 | 54 | wild | wild | 4, 4 | AD10E3 | fibroblast | epi, OSKMLshp53 | 46 XY | yes |
| SAD3 | male | 72 | 79 | wild | wild | 3, 4 | AD7E21 | fibroblast | epi, OSKMLshp53 | 46 XY | yes |
| SAD4 | female | 50 | 60 | wild | wild | 3, 4 | AD16E122 | fibroblast | epi, OSKMLshp53 | 46 XX | yes |
| HC1 | female | — | 36 | wild | wild | 3, 3 | 409B2 | fibroblast | epi, OSKMLshp53 | 46 XX | yes |
| HC2 | female | — | 51 | wild | wild | 2, 3 | N112E14 | fibroblast | epi, OSKMLshp53 | 46 XX | yes |
| HC3 | female | — | 69 | wild | wild | 3, 3 | N114E223 | fibroblast | epi, OSKMLshp53 | 46 XX | yes |
| HC4 | male | — | 47 | wild | wild | 3, 3 | hC6B | lymphocyte | epi, OSKMLshp53 | 46 XY | yes |

Lastly, BCroT and BCiP were orally administered to wild-type ICR mouse, and changes in the intracerebral Aβ amount 16 hr later were examined (FIG. 3g). The dose was converted to the clinically-used dose based on the body weight and examined at 5-fold and 25-fold amounts of the dose. The BCroT cocktail in the clinically-used dose showed a sufficient decrease in Aβ42 and Aβ42/40 ratio. On the other hand, the BCiP cocktail showed a decrease in Aβ42 and Aβ42/40 ratio at, by contrast, 5-fold and 25-fold amounts of the clinically-used dose (FIG. 3h).

Figure 11:
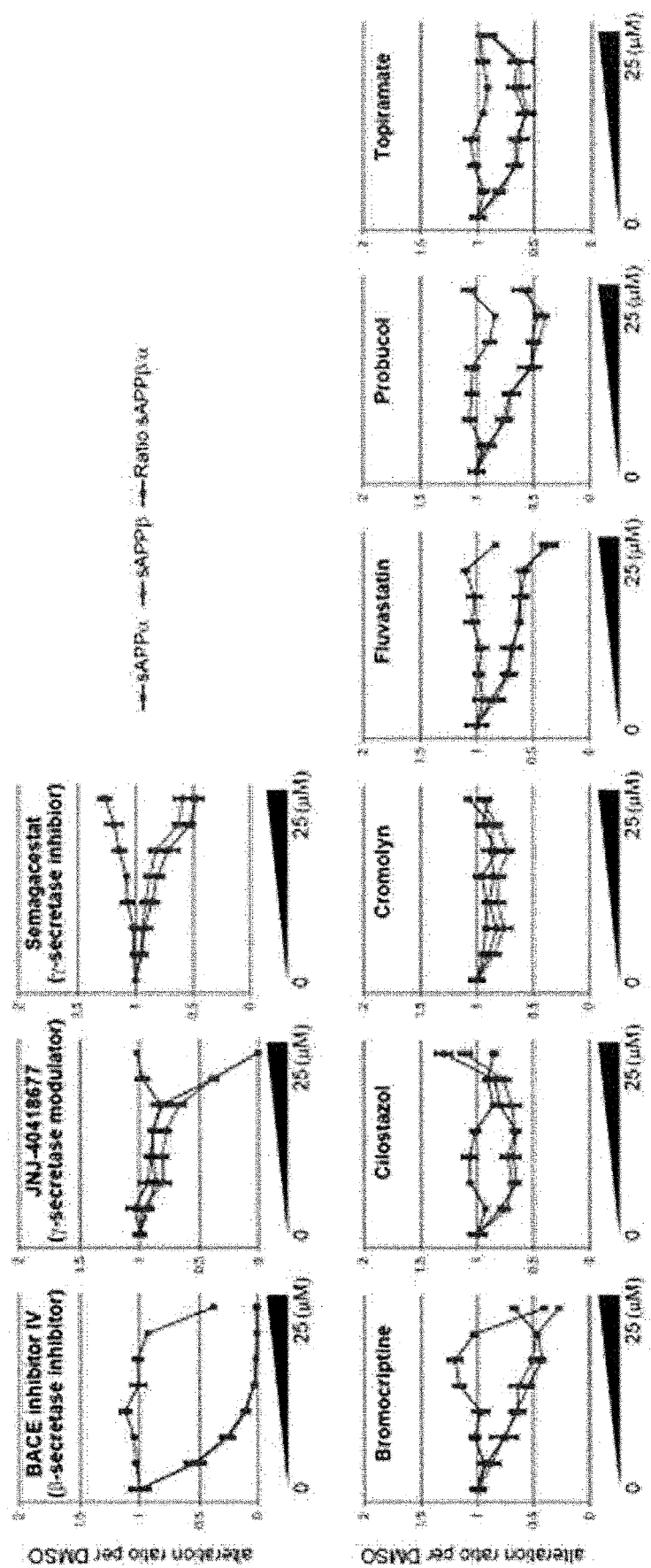
FIG. 11 FIG. 11 shows graphs showing dose-dependent changes in sAPPα, sAPPβ, sAPPβ/α ratio when BACE inhibitor IV, JNJ-40418677, semagacestat, Bromocriptine, Cilostazol, Cromolyn, Fluvastatin, Probucol, Topiramate were added.

6 kinds of the selected best existing drugs have clear information of safety, concentration suitable for use, side effects and the like, and show central nervous system permeability. The present invention has clarified a direct effect of the best existing drugs on AD nerve cells. Bromocriptine is classified in β-secretase inhibitor (BSI) group 1 by fingerprint (FIG. 2b) and suggested to have a BSI-like action also from the sAPP metabolism (Table 2, FIG. 11). On the other hand, since amphetamine, dopamine, ergot dopamine agonist show effects along with Bromocriptine, it was found that Aβ suppressive effect by dopamine series can be expected.

As shown in this Example, it was clarified that experimental results using mice and cell lines forcibly expressing AD causative genes at non-physiological expression levels and results of efficacy study using cerebral cortex nerve cell derived from human iPS cell at physiological gene expression levels are different. That is, studies using cerebral cortex nerve cell derived from human iPS cells are useful for a more appropriate efficacy evaluation. In the future, confirmation of effectiveness by using human nerve cells can be performed more precisely by further increasing the number of human iPS cells to be used for the efficacy evaluation at the final stage. It has the possibility of becoming an important step in drug discovery and development as an in vitro clinical trial that can evaluate efficacy by using nerve cells derived from human iPS cell before reaching Phase 1 trial (safety assessment in a small number of healthy subjects) and Phase 2 trial (safety and efficacy evaluation in a small number of patients) of current clinical trials.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

This application is based on a patent application No. 2015-257706 filed in Japan (filing date: Dec. 29, 2015), the contents of which are incorporated in full herein by reference.

INDUSTRIAL APPLICABILITY

The compounds described in Table 1 have superior effects in improving pathological changes of Aβ in AD, such as a decrease in the Aβ42/40 ratio, in nerve cells derived from AD patients.

Moreover, as a result of clustering these compounds based on the similarity of the molecular structure, it has been found that, by using a combination of two or more kinds of compounds belonging to different clusters, an additive improvement in efficacy is obtained as compared to single use of each compound. All of the compounds described in Table 1 have already been approved as pharmaceutical products for indications other than AD and marketed, and information relating to the safety and pharmacokinetics thereof has been accumulated.

Therefore, using a combination of two or more kinds of compounds belonging to different clusters and described in Table 1, Aβ pathology can be improved safely and effectively in AD patients, and it is extremely useful since intervention as a pre-emptive treatment for people at risk of AD who do not have clinical symptoms but have been judged positive by amyloid test can be expected.

The invention claimed is:

1. A method for reducing Aβ42/Aβ40 ratio in the brain of a subject, comprising administering to the subject an effective amount of each of bromocriptine and topiramate, wherein
  the effective amount of each of bromocriptine and topiramate is not more than a maximum nontoxic dose of each of bromocriptine and topiramate, and
  the Aβ42/Aβ40 ratio in the brain of the subject is reduced relative to the Aβ42/Aβ40 ratio in the brain of the subject in the absence of administering bromocriptine and topiramate to the subject.

2. The method according to claim 1, further comprising administering to the subject an effective amount of cromolyn, wherein the effective amount of each of bromocriptine, topiramate, and cromolyn is a clinically-used dose of each compound.

3. The method of claim 2, where the method is for treating Alzheimer's disease in the subject.

4. The method of claim 1, wherein the method is for treating Alzheimer's disease in the subject.

* * * * *